US012746053B2

(12) United States Patent
Frey et al.

(10) Patent No.: US 12,746,053 B2
(45) Date of Patent: Sep. 29, 2026

(54) ELECTROSURGICAL DEVICE AND METHOD OF USE

(71) Applicant: Stryker European Operations Limited, Cork (IE)

(72) Inventors: Laura Constance Frey, Belfast (IE); Scott McFarland, Greenisland (IE); Paul Sheridan, Wexford (IE); Micheal Burke, Cork (IE); Fernando Erismann, Sacramento, CA (US)

(73) Assignee: Stryker European Operations Limited, Carrigtwohohill (IE)

( * ) Notice: Subject to any disclaimer, the term of this patent is extended or adjusted under 35 U.S.C. 154(b) by 830 days.

(21) Appl. No.: 18/044,301

(22) PCT Filed: Sep. 9, 2021

(86) PCT No.: PCT/IB2021/000620
§ 371 (c)(1),
(2) Date: Mar. 7, 2023

(87) PCT Pub. No.: WO2022/053870
PCT Pub. Date: Mar. 17, 2022

(65) Prior Publication Data

US 2023/0346503 A1 Nov. 2, 2023

Related U.S. Application Data

(60) Provisional application No. 63/211,876, filed on Jun. 17, 2021, provisional application No. 63/076,089, filed on Sep. 9, 2020.

(51) Int. Cl.
*A61B 18/14* (2006.01)
*A61B 18/00* (2006.01)
(Continued)

(52) U.S. Cl.
CPC .......... *A61B 18/1402* (2013.01); *A61B 18/00* (2013.01); *A61B 90/30* (2016.02);
(Continued)

(58) Field of Classification Search
CPC ..... A61B 18/1402; A61B 18/00; A61B 90/30; A61B 2090/309; A61B 2017/00907;
(Continued)

(56) References Cited

U.S. PATENT DOCUMENTS

| | | |
|---|---|---|
| 6,090,107 A | 7/2000 | Brogmeier et al. |
| 6,511,479 B2 | 1/2003 | Gentelia et al. |

(Continued)

FOREIGN PATENT DOCUMENTS

| | | |
|---|---|---|
| CN | 209032624 | 6/2019 |
| EP | 0085658 | 8/1983 |
| WO | 2020211797 | 10/2020 |

OTHER PUBLICATIONS

International Search Report mailed on Jan. 25, 2022, issued in connection with International Application No. PCT/IB2021/000620, filed on Sep. 9, 2021, 5 pages.

(Continued)

*Primary Examiner* — Sameh R Boles
(74) *Attorney, Agent, or Firm* — McDonnell Boehnen Hulbert & Berghoff LLP

(57) ABSTRACT

In an example, an electrosurgical device includes a housing having a proximal end and a distal end, an electrosurgical electrode extending in a distal direction from the distal end of the housing, a plurality of light sources in the housing, and an optical lens assembly including a plurality of optical components that are (i) coupled to each other at a distal end of the optical lens assembly and (ii) separated from each other at a proximal end of the optical lens assembly. Each optical component includes a proximal reflector surface and
(Continued)

a distal transmission surface. Each proximal reflector surface extends distally from a respective light source and has an aspheric shape that is configured to substantially collimate the light reflected by the proximal reflector surface. Each distal transmission surface is configured to output the light from the optical component in the distal direction.

19 Claims, 24 Drawing Sheets

(51) Int. Cl.
*A61B 90/30* (2016.01)
*A61B 17/00* (2006.01)

(52) U.S. Cl.
CPC ............... *A61B 2017/00907* (2013.01); *A61B 2017/00991* (2013.01); *A61B 2018/00202* (2013.01); *A61B 2018/00589* (2013.01); *A61B 2018/00607* (2013.01); *A61B 2090/309* (2016.02); *A61B 2218/008* (2013.01)

(58) Field of Classification Search
CPC ........... A61B 2017/00991; A61B 2018/00202; A61B 2018/00589; A61B 2018/00607; A61B 2218/008
See application file for complete search history.

(56) References Cited

U.S. PATENT DOCUMENTS

| | | | |
|---|---|---|---|
| 8,449,540 | B2 | 5/2013 | Sartor et al. |
| 8,632,537 | B2 | 1/2014 | McNall, III et al. |
| 8,690,872 | B2 | 4/2014 | Jayaraj |
| 8,895,133 | B2 | 11/2014 | Nesbitt |
| 8,940,357 | B2 | 1/2015 | Nesbitt |
| 8,979,842 | B2 | 3/2015 | McNall, III et al. |
| 8,998,899 | B2 | 4/2015 | Shiev et al. |
| 9,237,922 | B2 | 1/2016 | Bromley et al. |
| 9,326,810 | B2 | 5/2016 | Shiev et al. |
| 9,375,253 | B2 | 6/2016 | Greep et al. |
| 9,486,562 | B2 | 11/2016 | Minksoff et al. |
| 9,750,855 | B2 | 9/2017 | Minksoff et al. |
| 9,974,527 | B2 | 5/2018 | Robinson |
| 10,064,675 | B2 | 9/2018 | Rencher et al. |
| 10,080,600 | B2 | 9/2018 | Jadhav et al. |
| 10,136,960 | B2 | 11/2018 | Fleenor |
| 10,188,393 | B2 | 1/2019 | Smith et al. |
| 10,363,088 | B2 | 7/2019 | Houser |
| 10,433,898 | B2 | 10/2019 | Borgmeier et al. |
| 10,433,899 | B2 | 10/2019 | Borgmeier et al. |
| 10,456,190 | B2 | 10/2019 | Vayser et al. |
| 10,492,787 | B2 | 12/2019 | Smith et al. |
| 10,499,974 | B2 | 12/2019 | Heim et al. |
| 10,765,472 | B2 | 9/2020 | Greep et al. |
| 10,806,504 | B2 | 10/2020 | Hubelbank |
| 10,881,444 | B2 | 1/2021 | Rencher et al. |
| 11,241,279 | B2 | 2/2022 | Ineson |
| 11,246,651 | B2 | 2/2022 | Cosmescu |
| 11,337,751 | B2 | 5/2022 | Choi |
| 11,406,445 | B2 | 8/2022 | Miller et al. |
| 11,589,917 | B2 | 2/2023 | Shvestsov et al. |
| 11,660,137 | B2 | 5/2023 | Davies et al. |
| 11,672,591 | B2 | 6/2023 | Hubelbank |
| 11,717,373 | B2 | 8/2023 | Greeley et al. |
| 11,751,935 | B2 | 9/2023 | Cosmescu |
| 11,751,942 | B2 | 9/2023 | Greeley et al. |
| 11,864,819 | B2 | 1/2024 | Ineson |
| 11,896,291 | B2 | 2/2024 | Helliger |
| 11,937,865 | B2 | 3/2024 | Simonsen |
| 12,082,869 | B2 | 9/2024 | Simonsen |
| 12,402,931 | B2 | 9/2025 | Frey et al. |
| 12,446,947 | B2 | 10/2025 | Frey et al. |
| 12,465,417 | B2 | 11/2025 | Simonsen |
| 2011/0201889 | A1 | 8/2011 | Vayser et al. |
| 2014/0257273 | A1 | 9/2014 | Cosmescu |
| 2014/0276763 | A1 | 9/2014 | Greep et al. |
| 2014/0276770 | A1 | 9/2014 | Ellman |
| 2016/0157920 | A1 | 6/2016 | Vayser et al. |
| 2018/0078301 | A1 | 3/2018 | Vayser |
| 2018/0333201 | A1 | 11/2018 | Greep et al. |
| 2019/0000470 | A1 | 1/2019 | Yates et al. |
| 2019/0110832 | A1 | 4/2019 | Simonsen |
| 2019/0201023 | A1 | 7/2019 | Shelton et al. |
| 2019/0216539 | A1 | 7/2019 | Choi |
| 2019/0321093 | A1 | 10/2019 | Greeley et al. |
| 2019/0380805 | A1* | 12/2019 | Greeley ................. A61B 90/30 |
| 2020/0155231 | A1 | 5/2020 | Greep et al. |
| 2020/0246057 | A1 | 8/2020 | Park |
| 2021/0338310 | A1 | 11/2021 | Zagatsky |
| 2022/0226037 | A1 | 7/2022 | Buckley et al. |
| 2022/0257302 | A1 | 8/2022 | Brandt et al. |
| 2023/0107451 | A1 | 4/2023 | Sims |
| 2023/0112770 | A1 | 4/2023 | Shen et al. |
| 2023/0139522 | A1 | 5/2023 | Knopf et al. |
| 2023/0233248 | A1 | 7/2023 | Dickson et al. |
| 2023/0293227 | A1 | 9/2023 | Cosmescu |
| 2023/0301703 | A1 | 9/2023 | Buckley et al. |
| 2023/0320777 | A1 | 10/2023 | Sims et al. |

OTHER PUBLICATIONS

Written Opinion mailed on Jan. 25, 2022, issued in connection with International Application No. PCT/IB2021/000620, filed on Sep. 9, 2021, 8 pages.
International Search Report and Written Opinion issued by the European Patent Office in international application No. PCT/IB2021/000610 dated Mar. 21, 2022.
International Search Report and Written Opinion issued by the European Patent Office in international application No. PCT/IB2023/000272 dated Oct. 4, 2023.

* cited by examiner

ELECTROSURGICAL DEVICE AND METHOD OF USE

CROSS-REFERENCE TO RELATED APPLICATIONS

This application is the US national phase under 35 U.S.C. § 371 of International Application No. PCT/IB2021/000620, filed Sep. 9, 2021, which claims the benefit of U.S. Provisional Application No. 63/076,089, filed Sep. 9, 2020, and U.S. Provisional Application No. 63/211,876, filed Jun. 17, 2021, the contents of which are hereby incorporated by reference in their entirety.

FIELD

The present disclosure generally relates to electrosurgical devices and, more specifically, to electrosurgical devices and the methods for illuminating a surgical site during an electrosurgical procedure.

BACKGROUND

Electrosurgery involves applying a radio frequency (RF) electric current (also referred to as electrosurgical energy) to biological tissue to cut, coagulate, or modify the biological tissue during an electrosurgical procedure. Specifically, an electrosurgical generator generates and provides the electric current to an active electrode, which applies the electric current (and, thus, electrical power) to the tissue. The electric current passes through the tissue and returns to the generator via a return electrode (also referred to as a "dispersive electrode"). As the electric current passes through the tissue, an impedance of the tissue converts a portion of the electric current into thermal energy (e.g., via the principles of resistive heating), which increases a temperature of the tissue and induces modifications to the tissue (e.g., cutting, coagulating, ablating, and/or sealing the tissue).

SUMMARY

In an example, an electrosurgical device is described. The electrosurgical device includes a housing having a proximal end and a distal end. The electrosurgical device also includes an electrosurgical electrode extending in a distal direction from the distal end of the housing, and a plurality of light sources in the housing. The plurality of light sources can be configured to generate light.

Additionally, the electrosurgical device can include an optical lens assembly having a proximal end and a distal end. The optical lens assembly can include a plurality of optical components that are (i) coupled to each other at the distal end of the optical lens assembly and (ii) separated from each other at the proximal end of the optical lens assembly. Each optical component is optically coupled to a respective light source of the plurality of light sources. Each optical component includes a proximal reflector surface extending distally from the respective light source that is optically coupled to the optical component and a distal transmission surface at the distal end of the optical lens assembly. The proximal reflector surface is configured to reflect light emitted by the respective light source toward the distal end. The proximal reflective surface can have an aspheric shape that is configured to substantially collimate the light reflected by the proximal reflector surface. The distal transmission surface is configured to output the light from the optical component in the distal direction.

In another example, a process for operating an electrosurgical device is described. The process includes providing an electrosurgical device at block 2410. The electrosurgical device can include a housing having a proximal end and a distal end. The electrosurgical device can also include an electrosurgical electrode extending in a distal direction from the distal end of the housing, and a plurality of light sources in the housing. The plurality of light sources can be configured to generate light.

Additionally, the electrosurgical device can include an optical lens assembly having a proximal end and a distal end. The optical lens assembly can include a plurality of optical components that are (i) coupled to each other at the distal end of the optical lens assembly and (ii) separated from each other at the proximal end of the optical lens assembly. Each optical component is optically coupled to a respective light source of the plurality of light sources. Each optical component includes a proximal reflector surface extending distally from the respective light source that is optically coupled to the optical component and a distal transmission surface at the distal end of the optical lens assembly. The proximal reflector surface is configured to reflect light emitted by the respective light source toward the distal end. The proximal reflective surface can have an aspheric shape that is configured to substantially collimate the light reflected by the proximal reflector surface. The distal transmission surface is configured to output the light from the optical component in the distal direction.

The process also includes emitting, by the plurality of light sources, the light. After emitting the light, the process includes transmitting the light through each optical component by: (i) reflecting, by the proximal reflector surface of the optical component, the light in a substantially collimated manner toward the distal end, and (ii) outputting, by the distal transmission surface of the optical component, the light in the distal direction.

The process also includes rotating the shaft relative to the housing to cause corresponding rotation of the electrosurgical electrode relative to the housing. The process further includes supplying electrosurgical energy from the shaft to the electrosurgical electrode.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Figure 1:
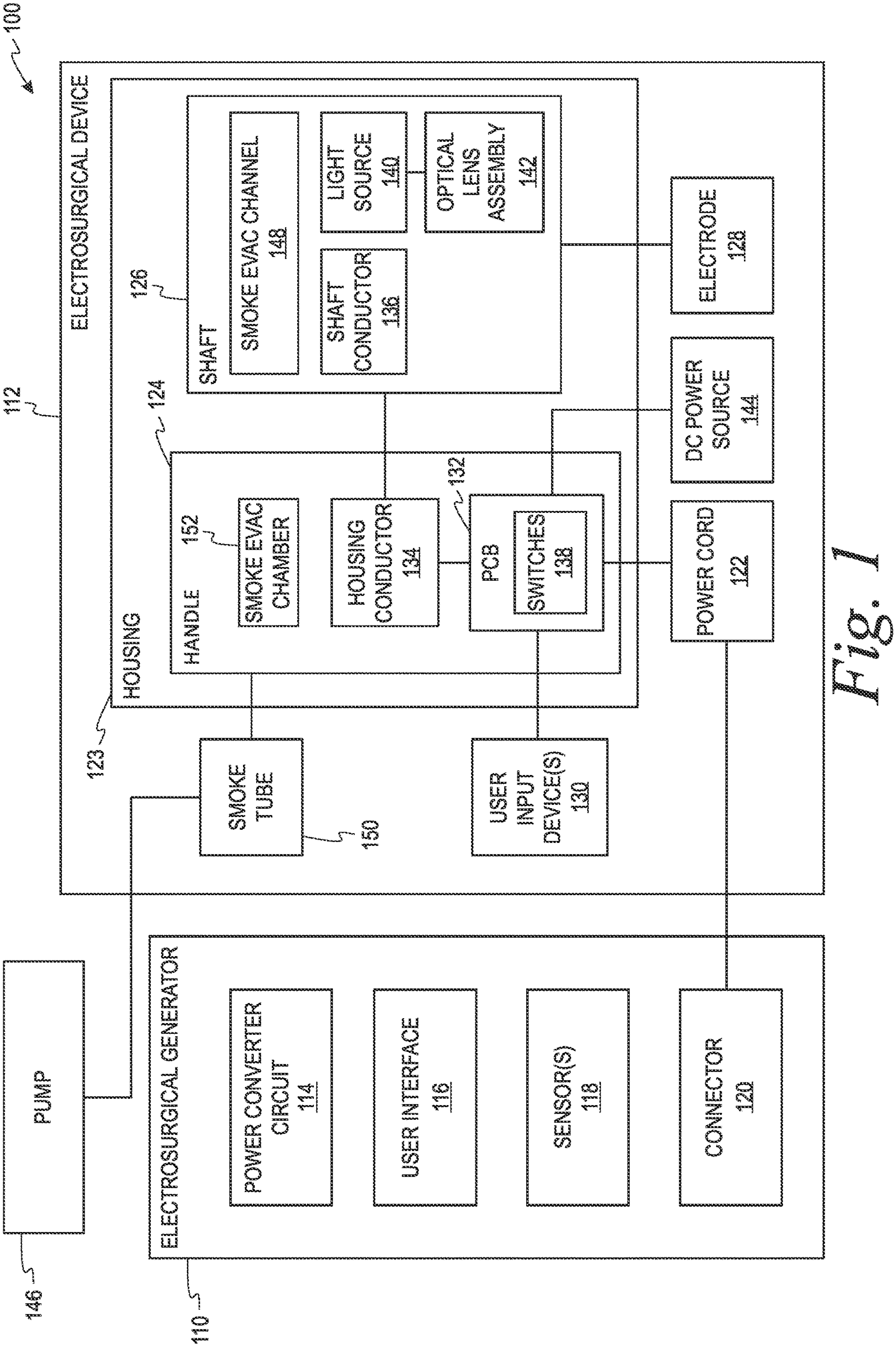
FIG. 1 depicts a simplified block diagram of an electrosurgical system, according to an example.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

By the term "approximately" or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As noted above, an electrosurgical device can use electrical energy supplied by an electrosurgical generator to apply electrosurgical energy from an electrosurgical electrode to a tissue. To help a practioner better visualize a surgical site while performing electrosurgery, the electrosurgical device can include features that provide for transmitting light in a distal direction to illuminate the surgical site. For example, the electrosurgical device can include one or more optical features that transmit light along and/or around the electrosurgical electrode to illuminate the surgical site.

Although providing the electrosurgical device with optical features for transmitting light can be beneficial, the optical features occupy space within or on the electrosurgical device. This can present certain challenges. For instance, it can be beneficial to limit or reduce a size of the electrosurgical device to provide greater access to small surgical cavities and/or mitigate the electrosurgical device impairing a line of sight to the electrosurgical electrode and/or the surgical site. These space constraint considerations may be further exacerbated in implementations in which the electrosurgical device includes other space-occupying features such as, for example, features for evacuating surgical smoke from the surgical site.

A further challenge is to achieve a quality of light emission in the relatively small space available. Indeed, it may be desirable to provide the light around a circumference of the electrosurgical electrode. And it may be beneficial to do so while mitigating shadows caused by the electrosurgical electrode. Further, it can be beneficial to reduce light loss along a light transmission path between a light source and a point at which the light is output from the electrosurgical device. For instance, reducing light loss can help to reduce power requirements for operating the light source and/or reduce heat.

The present application provides for an optical lens assembly that can be incorporated into an electrosurgical device to address one or more of the challenges described above.

Referring now to FIG. 1, an electrosurgical system 100 is shown according to an example. As shown in FIG. 1, the electrosurgical system 100 includes an electrosurgical generator 110 and an electrosurgical device 112. In general, the electrosurgical generator 110 can generate electrosurgical energy that is suitable for performing electrosurgery on a patient. For instance, the electrosurgical generator 110 can include a power converter circuit 114 that can convert a grid power to electrosurgical energy such as, for example, a radio frequency (RF) output power. As an example, the power converter circuit 114 can include one or more electrical components (e.g., one or more transformers) that can control a voltage, a current, and/or a frequency of the electrosurgical energy.

Within examples, the electrosurgical generator 110 can include a user interface 116 that can receive one or more inputs from a user and/or provide one or more outputs to the user. As examples, the user interface 116 can include one or more buttons, one or more switches, one or more dials, one or more keypads, one or more touchscreens, one or more display screens, one or more indicator lights, one or more speakers, and/or one or more haptic output devices.

In an example, the user interface 116 can be operable to select a mode of operation from among a plurality of modes of operation for the electrosurgical generator 110. As examples, the modes of operation can include a cutting mode, a coagulating mode, an ablating mode, and/or a sealing mode. Combinations of these waveforms can also be formed to create blended modes. In one implementation, the modes of operation can correspond to respective waveforms for the electrosurgical energy. As such, in this implementation, the electrosurgical generator 110 can generate the electrosurgical energy with a waveform selected from a plurality of waveforms based, at least in part, on the mode of operation selected using the user interface 116.

The electrosurgical generator 110 can also include one or more sensors 118 that can sense one or more conditions related to the electrosurgical energy and/or the target tissue. As examples, the sensor(s) 118 can include one or more current sensors, one or more voltage sensors, one or more temperature sensors, and/or one or more bioimpedance sensors. Within examples, the electrosurgical generator 110 can additionally or alternatively generate the electrosurgical energy with an amount of electrosurgical energy (e.g., an electrical power) and/or a waveform selected from among the plurality of waveforms based on one or more parameters related to the condition(s) sensed by the sensor(s) 118.

In one example, the electrosurgical energy can have a frequency that is greater than approximately 100 kilohertz (kHz) to reduce (or avoid) stimulating a muscle and/or a nerve near the target tissue. In another example, the electrosurgical energy can have a frequency that is between approximately 300 kHz and approximately 500 kHz.

In FIG. 1, the electrosurgical generator 110 also includes a connector 120 that can facilitate coupling the electrosurgical generator 110 to the electrosurgical device 112. For example, the electrosurgical device 112 can include a power cord 122 having a plug, which can be coupled to a socket of the connector 120 of the electrosurgical generator 110. In this arrangement, the electrosurgical generator 110 can supply the electrosurgical energy to the electrosurgical device 112 via the coupling between the connector 120 of the electrosurgical generator 110 and the power cord 122 of the electrosurgical device 112.

As shown in FIG. 1, the electrosurgical device 112 can include a housing 123. The housing 123 can be an elongated structure in and/or on which components of the electrosurgical device 112 can be disposed. In some examples, the housing 123 can be an integral, monolithic structure. In other examples the housing 123 can include a plurality of structures that are coupled to each other.

In FIG. 1, the housing 123 includes a handle 124 that defines an interior bore, a shaft 126 extending in a distal direction from the handle 124, and an electrosurgical electrode 128 coupled to the shaft 126. In general, the handle 124 can be configured to facilitate a user gripping and manipulating the electrosurgical device 112 while performing electrosurgery. For example, the handle 124 can have a shape and/or a size that can facilitate a user performing electrosurgery by manipulating the electrosurgical device 112 using a single hand. In one implementation, the handle 124 can have a shape and/or a size that facilitates the user holding the electrosurgical device 112 in a writing utensil gripping manner (e.g., the electrosurgical device 112 can be an electrosurgical pencil).

Additionally, for example, the handle 124 and/or the shaft 126 can be constructed from one or more materials that are electrical insulators (e.g., a plastic material). This can facilitate insulating the user from the electrosurgical energy flowing through the electrosurgical device 112 while performing the electrosurgery.

In some implementations, the shaft 126 can be coupled to the handle 124 in a fixed and non-moveable manner. This may simplify manufacturing and reduce a cost of manufacture by, for instance, simplifying electrical connections that may otherwise need to account for movement of the shaft 126 and the handle 124 relative to each other (e.g., by omitting slip ring electrical contacts and/or sliding electrical contacts). In one example, the handle 124 and the shaft 126 can be formed as a single, monolithic structure such that the shaft 126 and the handle 124 are fixed and non-moveable relative to each other. In another example, the handle 124 and the shaft 126 can be fixedly coupled to each other by a welding coupling, an adhesive coupling, and/or another coupling that prevents movement between the handle 124 and the shaft 126.

In other implementations, the shaft 126 can be telescopically moveable relative to the handle 124. For example, the shaft 126 can be telescopically moveable in the interior bore defined by the handle 124 to extend the shaft 126 in the distal direction and retract the shaft 126 in a proximal direction relative to the handle 124 (e.g., movable along a longitudinal axis of the electrosurgical device 112). In some examples, the electrosurgical electrode 128 is coupled to the shaft 126 and, thus, the electrosurgical electrode 128 can move together with the shaft 126 in an axial direction along the longitudinal axis relative to the handle 124. This can provide for adjusting a length of the electrosurgical device 112, which can facilitate performing electrosurgery at a plurality of different depths within tissue (e.g., due to different anatomical shapes and/or sizes of patients) and/or at a plurality of different angles.

In some implementations, the electrosurgical electrode 128 can additionally or alternatively be rotatable about an axis of rotation that is parallel to the longitudinal axis of the electrosurgical device 112. In some examples, the electrosurgical electrode 128 can be rotatable relative to the handle 124 and the shaft 126. In other examples, the electrosurgical electrode 128 can be rotationally fixed relative to the shaft 126 such that the shaft 126 and the electrosurgical electrode 128 are rotatable together relative to the handle 124 and at least one additional component in an inner cavity defined by the shaft 126. Rotating the electrosurgical electrode 128 relative to the handle 124 can facilitate adjusting an angle of the electrosurgical electrode 128 relative to one or more user input device(s) 130 of the electrosurgical device 112. In this arrangement, a user can comfortably grip the handle 124 in a position in which their fingers can comfortably operate the user input device(s) 130 while the electrosurgical electrode 128 is set at a rotational position selected from among a plurality of rotational positions relative to the handle 124 based on, for example, a location, a size, and/or a shape of a surgical site in which the user is operating.

In one implementation, the electrosurgical electrode 128 can be rotatable by more than 360 degrees relative to the handle 124. This can improve an ease of use by allowing an operator to freely rotate the electrosurgical electrode 128 without limitation. However, in other implementations, the electrosurgical electrode 128 can be rotatable by less than or equal to 360 degrees (e.g., rotatable by 180 degrees or rotatable by 360 degrees). This may still allow an operator to achieve a desired rotational arrangement, but with the possibility that the operator may rotate in first direction, reach a stop limiting further rotation, and then rotate back in a second direction to achieve the desired rotational arrangement.

Although it can be beneficial to provide for rotation of the monopolar electrosurgical electrode 128 relative to the handle 124 and/or the shaft 126, the monopolar electrosurgical electrode 128 can be rotationally fixed relative to the handle 124 and the shaft 126 in some implementations. This may, for example, help to simplify manufacturing and reduce a cost of manufacture by, for instance, simplifying electrical connections that may otherwise need to account for movement of the shaft 126 and the handle 124 relative to each other (e.g., by omitting slip ring electrical contacts and/or sliding electrical contacts).

The user input device(s) 130 can select between the modes of operation of the electrosurgical device 112 and/or the electrosurgical generator 110. For instance, in one implementation, the user input device(s) 130 can be configured to select between a cutting mode of operation and a coagulation mode of operation. Responsive to actuation of the user input device(s) 130 of the electrosurgical device 112, the electrosurgical device 112 can (i) receive the electrosurgical energy with a level of power and/or a waveform corresponding to the mode of operation selected via the user input device(s) 130 and (ii) supply the electrosurgical energy to the electrosurgical electrode 128.

In FIG. 1, the electrosurgical device 112 includes a plurality of electrical components that facilitate supplying the electrosurgical energy, which the electrosurgical device 112 receives from the electrosurgical generator 110, to the electrosurgical electrode 128. For example, the electrosurgical device 112 can include at least one electrical component selected from a group of electrical components including: a printed circuit board 132 (e.g., a flexible printed circuit board), a housing conductor 134, and/or a shaft conductors 136 that can provide a circuit for conducting the electrosurgical energy from the power cord 122 to the electrosurgical electrode 128. One or more of the electrical components can be positioned in the interior bore 125 defined by the handle 124 and/or in the inner cavity defined by the shaft 126.

Within examples, the user input device(s) 130 can include one or more buttons on an exterior surface of the handle 124. Each button of the user input device(s) 130 can be operable to actuate a respective one of a plurality of switches 138 of the printed circuit board 132. In general, the switches 138 and/or the printed circuit board 132 are operable to control a supply of the electrosurgical energy from the electrosurgical generator 110 to the electrosurgical electrode 128. For instance, in one implementation, when each button is operated (e.g., depressed), the respective switch 138 associated with the button can be actuated to cause the printed circuit board 132 to transmit a signal to the electrosurgical generator 110 and cause the electrosurgical generator 110 to responsively supply the electrosurgical energy with a level of power and/or a waveform corresponding to a mode of operation associated with the button. In another implementation, operating the button and thereby actuating the respective switch 138 associated with the button can close the switch 138 to complete a circuit to the electrosurgical generator 110 to cause the electrosurgical generator 110 to responsively supply the electrosurgical energy with a level of power and/or a waveform corresponding to a mode of operation associated with the button. In some examples of this implementation, the printed circuit board 132 can be omitted.

In both example implementations, the electrosurgical energy supplied by the electrosurgical generator 110 can be supplied from (i) the power cord 122, the printed circuit board 132, and/or the switches 138 to (ii) the electrosurgical electrode 128 by the housing conductor 134 and the shaft conductor 136. As such, as shown in FIG. 1, the printed circuit board 132 can be coupled to the power cord 122, the housing conductor 134 can be coupled to the printed circuit board 132 and the shaft conductor 136, and the shaft conductor 136 can be coupled to the electrosurgical electrode 128. In this arrangement, the housing conductor 134 can conduct the electrosurgical energy (supplied to the housing conductor 134 via the printed circuit board 132) to the shaft conductor 136, and the shaft conductor 136 can conduct the electrosurgical energy to the electrosurgical electrode 128.

In general, the housing conductor 134 and the shaft conductor 136 can each include one or more electrically conductive elements that provide an electrically conductive bus for supplying the electrosurgical energy to the electrosurgical electrode 128. More particularly, the housing conductor 134 can include one or more electrically conductive elements of the handle 124 that can supply the electrosurgical energy to the shaft conductor 136, and the shaft conductor 136 can include one or more electrically conductive elements of the shaft 126 that can supply the electrical energy from the housing conductor 134 to the electrosurgical electrode 128. In implementations in which the shaft 126 is movable and/or rotatable relative to the handle 124, the housing conductor 134 can engage the shaft conductor 136 to maintain an electrical coupling between the housing conductor 134, the shaft conductor 136, and the electrosurgical electrode 128 while (i) the shaft 126 and/or the electrosurgical electrode 128 telescopically moves relative to the handle 124, and/or (ii) the electrosurgical electrode 128 rotates relative to the handle 124.

Although the electrosurgical device 112 includes the user input device(s) 130 in FIG. 1, the user input device(s) 130 can be separate from the electrosurgical device 112 in another example. For instance, the user input device(s) 130 can additionally or alternatively include one or more foot pedals that are actuatable to control operation of the electrosurgical device 112 as described above. The foot pedal(s) can be communicatively coupled to the electrosurgical generator 110 to provide a signal responsive to actuation of the foot pedal(s).

As shown in FIG. 1, the electrosurgical device 112 can additionally include one or more light sources 140 that are configured to emit light. The light source(s) 140 can be optically coupled to an optical lens assembly 142, which is configured to receive the light emitted by the light source(s) 140 and transmit the light in a distal direction toward a surgical site to illuminate the surgical site while performing electrosurgery using the electrosurgical electrode 128. As described in further detail below with respect to FIGS. 4A-23 the optical lens assembly 142 can help to direct the light emitted by the light source 140 in the distal direction and thereby improve a quality of the light illuminating the surgical site.

In FIG. 1, the light source 140 can be coupled to the shaft 126. As such, the light source 140 can also move telescopically with the shaft 126 relative to the handle 124. However, in other examples, the light source 140 can be in the interior bore of the handle 124 and/or coupled to an exterior surface of the handle 124. As examples, the light source 140 can include one or more light emitting diodes (LEDs), organic light emitting diodes (OLEDs), optical fibers, non-fiber optic waveguides, and/or lenses. Additionally, for example, the light source 140 can include a light-emitting diode printed circuit board (LED PCB) having one or more light sources (e.g., LEDs). As described in further detail below, the LED PCB can include a PCB aperture, and one or more other components (e.g., the electrosurgical electrode 128) of the electrosurgical device 112 can extend through the aperture.

In implementations that include the light source 140, the user input device(s) 130, the printed circuit board 132, the switches 138, the housing conductor 134, and/or the shaft conductor 136 can additionally supply an electrical power from a direct current (DC) power source 144 to the light source 140. In one example, the DC power source 144 can include a battery disposed in the handle 124, the plug of the power cord 122, and/or a battery receptacle located along the power cord 122 between the handle 124 and the plug. Although the electrosurgical device 112 includes the DC power source 144 in FIG. 1, the DC power source 144 can be separate and distinct from the electrosurgical device 112 in other examples. For instance, in another example, the electrosurgical generator 110 can include the DC power source 144.

Additionally, in implementations that include the light source 140, the user input device(s) 130 can be operable to cause the light source 140 to emit the light. In one example, the user input device(s) 130 can include a button that independently controls the light source 140 separate from the button(s) that control the electrosurgical operational modes of the electrosurgical device 112. In another example, the user input device(s) 130 and the printed circuit board 132 can be configured such that operation of the button(s) that control the electrosurgical operational mode simultaneously control operation of the light source 140 (e.g., the light source 140 can be automatically actuated to emit light when a button is operated to apply the electrosurgical energy at the electrosurgical electrode 128).

As shown in FIG. 1, responsive to operation of the user input device(s) 130 to actuate the light source 140, the DC power source 144 can supply the electrical power (e.g., a DC voltage) to the light source 140 via the printed circuit board 132, the housing conductor 134, and/or the shaft conductor 136. In this implementation, one or more of the conductive elements of the housing conductor 134 can be configured to supply the electrical power from the DC power source 144 to the light source 140 and/or return the electrical power from the light source 140 to the DC power source 144. Accordingly, the housing conductor 134 can additionally or alternatively assist in providing electrical communication between the DC power source 144 and the light source 140 as the shaft 126 and the light source 140 telescopically move relative to the handle 124.

Although the user input device(s) 130 on the handle 124 can be operated to control the operation of the light source 140 in the examples described above, the light source 140 can be additionally or alternatively operated by one or more user input device(s) on the electrosurgical generator 110 (e.g., via the user interface 116) and/or on the plug of the power cord 122.

As noted above, the electrosurgical device 112 can additionally include features that provide for evacuating surgical smoke from a target tissue to a location external to the surgical site. Surgical smoke is a by-product of various surgical procedures. For example, during surgical procedures, surgical smoke may be generated as a by-product of electrosurgical units (ESU), lasers, electrocautery devices, ultrasonic devices, and/or other powered surgical instruments (e.g., bones saws and/or drills). In some instances, the surgical smoke may contain toxic gases and/or biological products that result from a destruction of tissue. Additionally, the surgical smoke may contain an unpleasant odor. For these and other reasons, many guidelines indicate that exposure of surgical personnel to surgical smoke should be reduced or minimized.

To reduce (or minimize) exposure to surgical smoke, a smoke evacuation system may be used during the surgical procedure. In general, the smoke evacuation system may include a suction pump 146 that can generate sufficient suction and/or vacuum pressure to draw the surgical smoke away from the surgical site. In some implementations, the smoke evacuation system may be coupled to an exhaust system (e.g., an in-wall exhaust system) that exhausts the surgical smoke out of an operating room. In other implementations, the smoke evacuation system may filter air containing the surgical smoke and return the air to the operating room. Within examples, the suction pump 146 and the electrosurgical generator 110 can be provided as separate devices or integrated in a single device (e.g., in a common housing).

As shown in FIG. 1, the shaft 126 can include a smoke evacuation channel 148 in the inner cavity of the shaft 126. The smoke evacuation channel 148 can also include a smoke inlet that can extend circumferentially around a center axis of a distal portion of the electrosurgical electrode 128. In this arrangement, the smoke inlet of the smoke evacuation channel can help to receive surgical smoke into the smoke evacuation channel 148 in all rotational alignments of the electrosurgical electrode 128 relative to the handle 124 and/or the electrosurgical device 112 relative to the target tissue. However, in another example, the smoke evacuation channel 148 can include one or more smoke inlets that do not extend circumferentially around the electrosurgical electrode 128.

In an example, the smoke evacuation channel 148 can include an outer tube that is separated from the optical lens assembly 142 by an air gap. For instance, the shaft 126 can include a plurality of standoffs that extend between the optical lens assembly 142 and the outer tube of the smoke evacuation channel 148 to provide the air gap between the outer tube and the optical lens assembly 142. In one implementation, the optical lens assembly 142 can include the standoffs such that the optical lens assembly 142 and the standoffs are formed as a single, monolithic structure. In another implementation, the standoffs can be formed as a single, monolithic structure with the outer tube of the smoke evacuation channel 148. In another implementation, the standoffs can be separate from the outer tube of the smoke evacuation channel 148 and the optical lens assembly 142.

Figure 2:
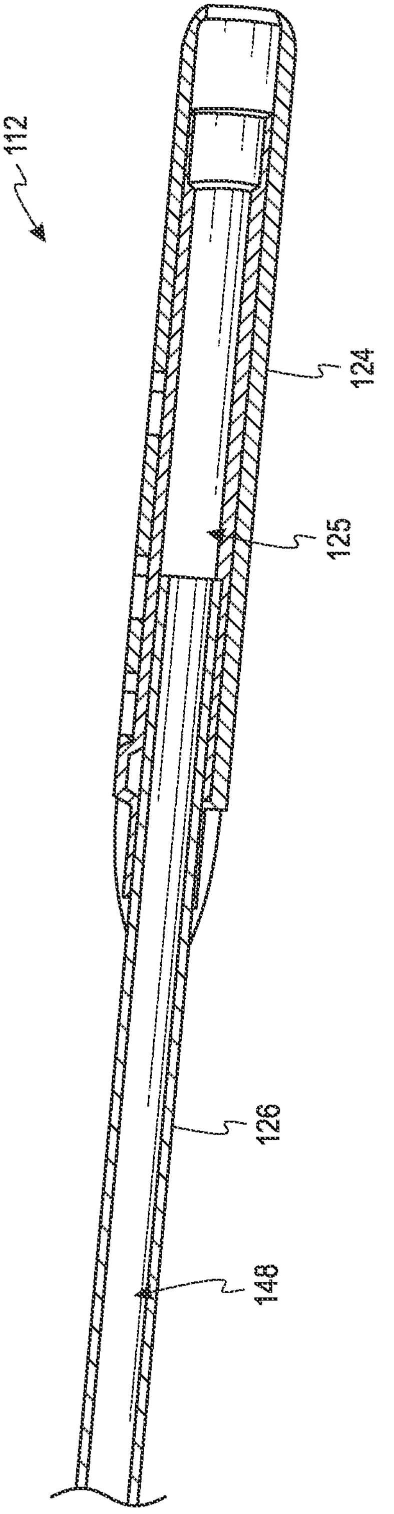
FIG. 2 depicts a cross-sectional view of an electrosurgical device, according to an example.

In an example, the smoke evacuation channel 148 of the shaft 126 defines a first portion of a smoke flow path, and an interior bore of the handle 124 defines a second portion of a smoke flow path. FIG. 2 illustrates a partial cross-sectional view of the electrosurgical device 112 according to an implementation of this example. In this arrangement, the surgical smoke can be received from the surgical site into the smoke evacuation channel 148 of the shaft 126, and flow proximally along the smoke evacuation channel 148 to the interior bore 125 of the handle 124. In the interior bore 125 of the handle 124, the smoke can further flow to a smoke tube 150 that is coupled to a proximal end of the handle 124 and configured to convey smoke from the handle 124 to the suction pump 146.

As noted above, the optical lens assembly 142 can help to direct the light emitted by the light source 140 in the distal direction and thereby improve a quality of the light illuminating the surgical site. The optical lens assembly 142 can be at a distal end of the shaft 126. In some examples, the optical lens assembly 142 can be arranged circumferentially around the electrosurgical electrode 128 to emit the light distally around all sides of the electrosurgical electrode 128. This can help to mitigate shadows and provide greater uniformity of illumination in all rotational alignments of the shaft 126 relative to the handle 124 and/or the electrosurgical device 112 relative to the target tissue.

In some implementations, the smoke evacuation channel 148 and the optical lens assembly 142 can be coaxial. For instance, the smoke evacuation channel 148 and the optical lens assembly 142 can each have a longitudinal axis that is aligned with a central axis of the shaft 126. It can be beneficial for efficient suction performance to arrange the smoke evacuation channel 148 such that a center axis of o the smoke evacuation channel 148 is aligned with the central axis of the shaft 126. Similarly, it can be beneficial to locate the electrosurgical electrode 128 in alignment with the central axis of the shaft 126 to provide, for example, better lines of sight in all rotational alignments and/or more intuitive handling.

Within examples, the optical lens assembly 142 can define a through-bore, and the smoke evacuation channel 48 and/or the electrosurgical electrode 128 can extend through the through-bore. In such an arrangement, the electrosurgical electrode 128 can be centered on the shaft 126, the smoke evacuation channel 148 can extend and receive smoke around the circumference of the electrosurgical electrode 128, and the optical lens assembly 142 can emit extend and emit light around the circumference of the electrosurgical electrode 128.

Figure 3:
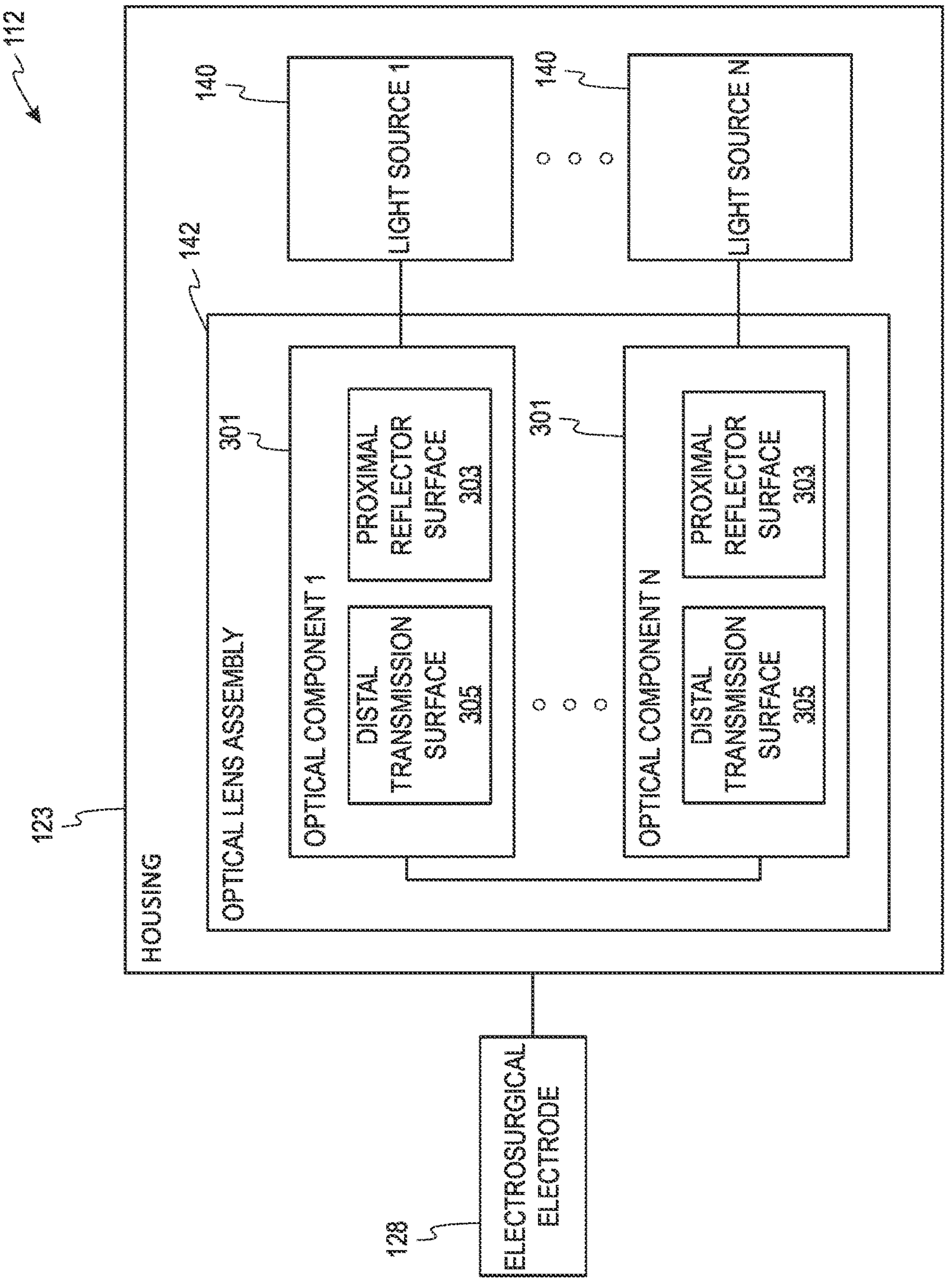
FIG. 3 depicts a simplified block diagram of an electrosurgical system, according to an example.

FIG. 3 depicts a simplified block diagram of the electrosurgical device 112 shown in FIG. 1 and including additional features of the optical lens assembly 142, according to an example. In FIG. 3, the electrosurgical system 100 includes the housing 123, the electrosurgical electrode 128, the plurality of light sources 140 in the housing 123, and the optical lens assembly 142. The housing 123 has a proximal end and a distal end, and the electrosurgical electrode 128 extends in a distal direction from the distal end of the housing 123.

Also, in FIG. 3, the optical lens assembly 142 has a proximal end and a distal end. The optical lens assembly 142 includes a plurality of optical components 301 that are (i) coupled to each other at the distal end of the optical lens assembly 142 and (ii) separated from each other at the proximal end of the optical lens assembly 142. Within examples, the plurality of optical components 301 are effectively not in optical communication with each other (e.g., less than approximately 10% of light from one optical component 301 passes through an adjacent one of the optical components 301). This can help to provide a relatively narrower beam of light. However, a portion of the light emitted by one of the optical components 301 can overlap with a portion of light emitted by another one of the optical components 301. This can provide for a broad beam of light as compared to an implementation in which the optical components 301 are not in optical communication.

In FIG. 3, the optical lens assembly 142 can include two or more optical components 301. More particularly, the optical lens assembly 142 can include a quantity of optical components equal to N, where N is an integer value that is greater than one. As shown in FIG. 3, each optical component 301 is optically coupled to a respective light source 140 of the plurality of light sources 140. As such, the light sources 140 can also include a quantity of light sources equal to N. In one implementation, the optical lens assembly 142 can include three or more optical components 301 and three or more light sources 140. This can help to distribute the optical components 301 around the longitudinal axis of the shaft 126 such that the optical lens assembly 142 can emit light in a distal direction and around the electrosurgical electrode 128 to (i) mitigate the formation of shadows and (ii) provide greater uniformity of illumination in all rotational alignments of the electrosurgical electrode 128 relative to the handle 124 and/or the electrosurgical device 112 relative to the target tissue.

As described in further detail below, at the proximal end of the optical lens assembly 142, each optical component 301 can define a cavity in which the respective light source 140 is located such that the light sources 140 are distal of a proximal-most surface of the optical lens assembly 142. This can help to better capture and transmit wide angle light rays emitted by the light sources 140 as compared to other optical lenses in which the light sources are located proximal to the proximal-most surface of an optical lens assembly. However, in some implementations, the light sources can be located proximal of the proximal-most surface of the optical lens assembly 142.

Each optical component 301 includes a proximal reflector surface 303 and a distal transmission surface 305. The proximal reflector surface 303 extends distally from the respective light source 140 that is optically coupled to the optical component 301. The proximal reflector surface 303 is configured to reflect light emitted by the respective light source 140 toward the distal end of the optical component 301. In some examples, the proximal reflector surface 303 can have a spherical shape or a parabolic shape that is configured to substantially collimate light reflected by the proximal reflector surface 303.

In other examples, the proximal reflective surface 303 has an aspheric shape that is configured to substantially collimate the light reflected by the proximal reflector surface 303. The aspheric shape of the proximal reflector surface 303 can provide greater efficiency and achieve a higher level of collimation of light than is possible with a parabolic reflective surface or a spherical reflective surface. In one example, the aspheric shape of the proximal reflector surface 303 can be defined by equation 1 below:

$$z(r) = C * r\hat{}2 / (1 + sqrt(1 - C\hat{}2 * (K+1) * r\hat{}2) + a4 * r\hat{}4 + a6 * r\hat{}6 + a8 * r\hat{}8 \quad \text{(eq. 1)}$$

where C=curvature, K=conic constant, a4, a6, and a8 are aspheric coefficients. Further, in an implementation, a proximal portion of the proximal reflector surface 303 can have a parabolic shape and a distal portion of the proximal reflector surface 303 can have the aspheric shape. This may also help to collimate relatively wide angle rays of light.

Within examples, the proximal reflector surface 303 can be a total internal reflection (TIR) reflector. For example, the proximal reflector surface 303 and the housing 123 can be separated from each other such that an air gap surrounds the proximal reflector surface 303. Arranging the proximal reflector surface 303 as a TIR reflector can help to mitigate additional manufacturing costs and/or biocompatibility requirements associated with metallic reflectors that are typically incorporated in many conventional light devices (e.g., flashlights).

The distal transmission surface 305 is at the distal end of the optical lens assembly 142. The distal transmission surface 305 is configured to output the light from the optical component 301 in the distal direction. Each distal transmission surface 305 of the optical lens assembly 142 can include one or more features for controlling the output of the light from the optical lens assembly 142. Within examples, at a plane that is distal of the distal end of the electrosurgical electrode 128, the light emitted by optical lens assembly 142 can have a substantially uniform intensity of light at each point in space. For instance, the light emitted by the optical lens assembly 142 can define a light pattern at the plane that is distal of the distal end of the electrosurgical electrode 128, and an intensity of the light at a weakest part of the light pattern can have an intensity that is at least 50 percent an intensity of the light at a strongest part of the light pattern.

In some examples, each distal transmission surface 305 can be an aspheric lens that is configured to provide the light in a substantially uniform manner. In one implementation, each distal transmission surface 305 can be partitioned into a plurality of zones, and light rays can be traced from each zone can be traced to the target plane. The aspheric surfaces can be configured such that a distribution of the light rays provide an approximately uniform level of irradiance within a defined area of the target plane. For instance, the aspheric lens can be designed by determining, using Snell's law and traces of the light rays, a lens surface angle for each zone and then curve fitting the angles to the aspheric sag equation (e.g., equation 1 above) to determine a continuous aspheric surface.

In another example, each distal transmission surface 305 can a Fresnel lens. For instance, the Fresnel lens can have a flat surface at a distal end. The flat surface at the distal end can define a plurality of rings that are concentric with each other, each ring can have a respective optical characteristic (e.g., Fresnel groove defined by a pitch, a depth, an angle, and/or a curvature), and the optical characteristics of the plurality of rings can differ from each other such that the flat surface at the distal end transmits light in a manner that approximates an aspheric lens (e.g., different rings can differ in at least one of the pitch, the depth, the angle, and/or the curvature of the Fresnel groove). This can help to improve focusing light at the distal transmission surface 305 while maintaining a relatively flat and compact shape.

In another example, the distal transmission surface 305 can include a plurality of lenslets at the distal end on one type of lens selected from among a group of lens types consisting of a spherical lens, an aspheric lens, and a Fresnel lens. The lenslets can further help to improve uniformity of light intensity. For example, the lenslets can include a plurality of small, spherical lenses arranged in a regular pattern. For instance, the pattern can be hexagonal (e.g., each lenslet has six sides) or rectangular (e.g., each lenslet has four sides) with adjacent lenslets abutting each other. Each small spherical lenslet creates an image of the source. So the lenslet array produces a plurality of images of the source. Because the lenslets include a plurality of lenses arranged close together, the images will overlap at least in part on top of each other, making it difficult for the human eye to discern a single image. As a result, the beam of light appears uniform and homogenous.

Figure 5A:
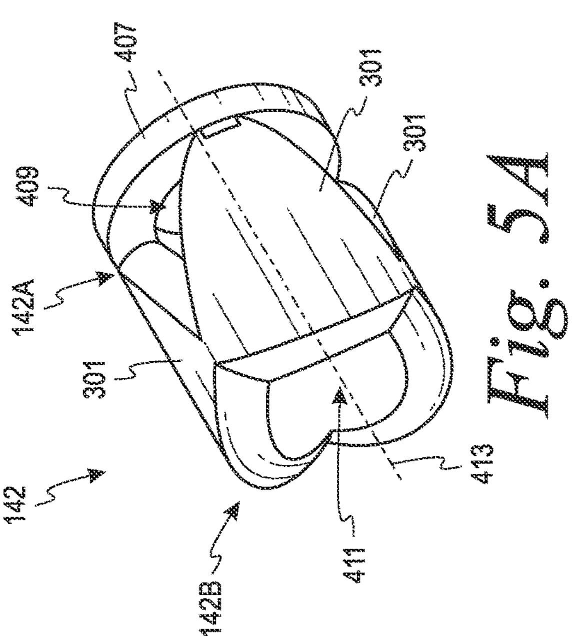
FIG. 5A depicts an implementation of the optical lens assembly shown in FIG. 3 and a light source, according to another example.
Figure 5B:
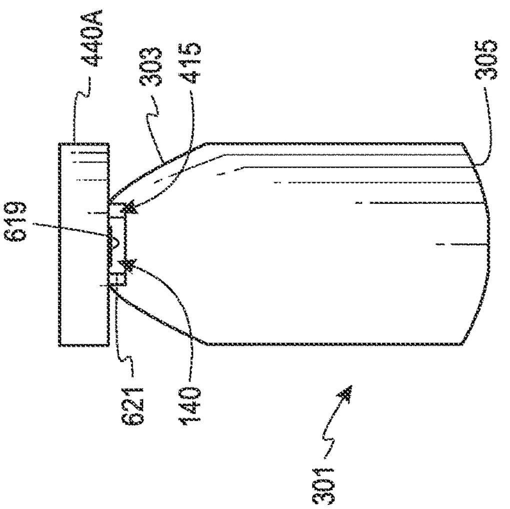
FIG. 5B depicts a cross-sectional view of an optical component of the optical lens assembly shown in FIG. 5, according to an example.
Figure 4A:
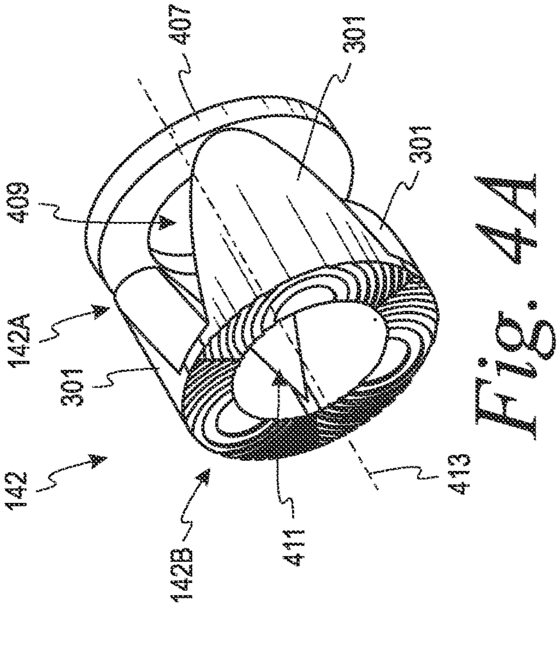
FIG. 4A depicts an implementation of the optical lens assembly shown in FIG. 3 and a light source, according to an example.

FIGS. 4A-5B depict two implementations of the optical lens assembly 142 of FIG. 3 according to examples. In particular, FIG. 4A and FIG. 5A depict an assembly of the optical lens assembly 142 and the light source 140 according to a first and second example implementations, respectively, and FIGS. 4B and 5B depict a cross-sectional view through one optical component 301 of the optical lens assembly 142 and the light source 140 in FIG. 4A and FIG. 5A, respectively.

As shown in FIGS. 4A-5B, the optical lens assembly 142 has the proximal end 142A and the distal end 142B. The optical lens assembly 142 also includes the optical components 301 that are (i) coupled to each other at the distal end 142B of the optical lens assembly 142 and (ii) separated from each other at the proximal end 142A of the optical lens assembly 142. In these examples, the optical components 301 are not in optical communication with each other. However, a portion of the light emitted by one of the optical components 301 can overlap with a portion of light emitted by another one of the optical components 301 to more uniformly distribute the light at the plane distal of the distal end of the electrosurgical electrode 128. In one example, the optical lens assembly 142 can be formed by a molding process.

In FIGS. 4A-5B, the optical lens assembly 142 includes three optical components 301 and three light sources 140. As noted above, this can help to distribute the optical components 301 around a longitudinal axis 413 of the shaft 126 such that the optical lens assembly 142 can emit light in a distal direction and around the electrosurgical electrode 128 to mitigate the formation of shadows. Additionally, for instance, three optical components 301 and three light sources 140 can provide a desired quality of light in a more compact arrangement and with lower power requirements than other implementations including a different quantity of optical components 301 and light sources 140. However, in other examples, the optical lens assembly 142 can include a different quantity of optical components 301 and light sources 140.

In the illustrated examples, the light sources 140 include a plurality of LEDs coupled to a LED PCB 407. The LED PCB 407 can be in the form of a ring having a PCB aperture 409 that extends entirely through LED PCB 407. The optical lens assembly 142 can also include a lens aperture 411 that defines a through-bore through the optical lens assembly 142. The PCB aperture 409 of the LED PCB 407 can be aligned with the lens aperture 411 of the optical lens assembly 142 such that one or more other components (e.g., the electrosurgical electrode 128 and/or the smoke evacuation channel 148) of the electrosurgical device 112 can extend through the LED PCB 407 and the optical lens assembly 142 with the LEDs located around a periphery of the component(s).

For instance, the light sources 140 can be arranged circumferentially around the longitudinal axis 413 of the electrosurgical electrode 128, where the longitudinal axis 413 extends between a proximal end of the electrosurgical electrode 128 and a distal end of the electrosurgical electrode 128. In FIGS. 4A-5B, the three light sources 140 are equally spaced around the longitudinal axis 413 of the electrosurgical electrode 128, and the lens aperture 411 defined by the optical lens assembly 142 has center axis that is collinear with the longitudinal axis 413 of the electrosurgical electrode 128. This can help to improve a uniformity of the light around the electrosurgical electrode 128.

Additionally, for instance, a suction tube defining the smoke evacuation channel 148 can extend through the PCB aperture 409 in the LED PCB 407 and the lens aperture 411 in the optical lens assembly 142. In this arrangement, the light sources 140 can be located around a circumference of the suction tube, and the distal end 142B of the optical lens assembly 142 can extend around the circumference of the suction tube. This can allow for evacuating smoke and emitting light around the circumference of the electrosurgical electrode 128.

As shown in FIGS. 4A and 5A, the optical lens assembly 142 includes an inner surface and an outer surface. The inner surface defines the lens aperture 411 and the through-bore of the optical lens assembly 142. In one example, between the proximal reflector surface 303 and the distal transmission surface 305, a cross-section of the optical lens assembly 142 has a circular shape at the inner surface and a non-circular shape at the outer surface. This can allow for the optical lens assembly 142 to rotate relative to a component extending through the through-bore of the optical lens assembly 142 while inhibiting rotation of the optical lens assembly 142 relative to a component adjacent to the outer surface. As examples, the non-circular shape can be an elliptical shape, a polygonal shape, and/or a non-polygonal shape.

In another example, the inner surface can have a non-circular cross-sectional shape while the outer surface has a circular shape to allow rotation of a peripherally disposed component and inhibit rotation of an internally disposed component relative to the optical lens assembly 142. In another example, both the inner surface and the outer surface can have a circular cross-sectional shape to allow rotation of adjacent components, or both the inner surface and the outer surface can have a non-circular shape to inhibit rotation of adjacent components.

Figure 4B:
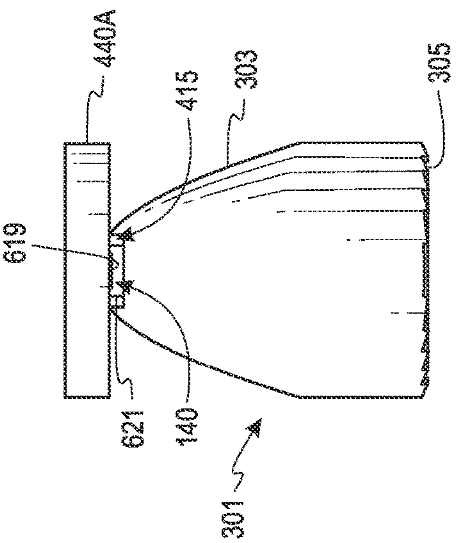
FIG. 4B depicts a cross-sectional view of an optical component of the optical lens assembly shown in FIG. 4, according to an example.

As shown in FIGS. 4B and 5B, at the proximal end 142A of the optical lens assembly 142, each optical component 301 can define a cavity 415 in which the respective light source 140 is located such that the light sources 140 are distal of a proximal-most surface of the optical lens assembly 142. Additionally, each optical component 301 is separated from the respective light source 140 optically coupled to the optical component 301 by an air gap. This can help to better capture and transmit wide angle light rays emitted by the light sources 140 as compared to other optical lenses in which the light sources are located proximal to the proximal-most surface of the optical lens assembly 142.

As shown in FIGS. 4A-5B, each optical component 301 includes the proximal reflector surface 303 and the distal transmission surface 305. The proximal reflector surface 303 extends distally from the respective light source 140 that is optically coupled to the optical component 301. The proximal reflector surface 303 is configured to reflect light emitted by the respective light source 140 toward the distal end of the optical component 301.

Also, in FIGS. 4A-5B, the proximal reflective surface 303 has an aspheric shape that is configured to substantially collimate the light reflected by the proximal reflector surface 303. The aspheric shape of the proximal reflector surface 303 can provide greater efficiency and achieve a higher level of collimation of light than is possible with a parabolic reflective surface or a spherical reflective surface. Further, in an implementation, a proximal portion of the proximal reflector surface 303 can have a parabolic shape and a distal portion of the proximal reflector surface 303 can have the aspheric shape. This may also help to collimate relatively wide angle rays of light.

As noted above, the proximal reflector surface 303 can be a total internal TIR reflector. For example, the proximal reflector surface 303 and the housing 123 can be separated from each other such that an air gap surrounds the proximal reflector surface 303. Arranging the proximal reflector surface 303 as a TIR reflector can help to mitigate additional manufacturing costs and/or biocompatibility requirements associated with metallic reflectors.

The distal transmission surface 305 is at the distal end 142B of the optical lens assembly 142. The distal transmission surface 305 is configured to output the light from the optical component 301 in the distal direction. As noted above, each distal transmission surface 305 of the optical lens assembly 142 can include one or more features for controlling the output of the light from the optical lens assembly 142. For example, each distal transmission surface 305 is a Fresnel lens in FIGS. 4A-4B, and each distal transmission surface 305 is an aspheric surface in FIGS. 5A-5B.

Figure 6:
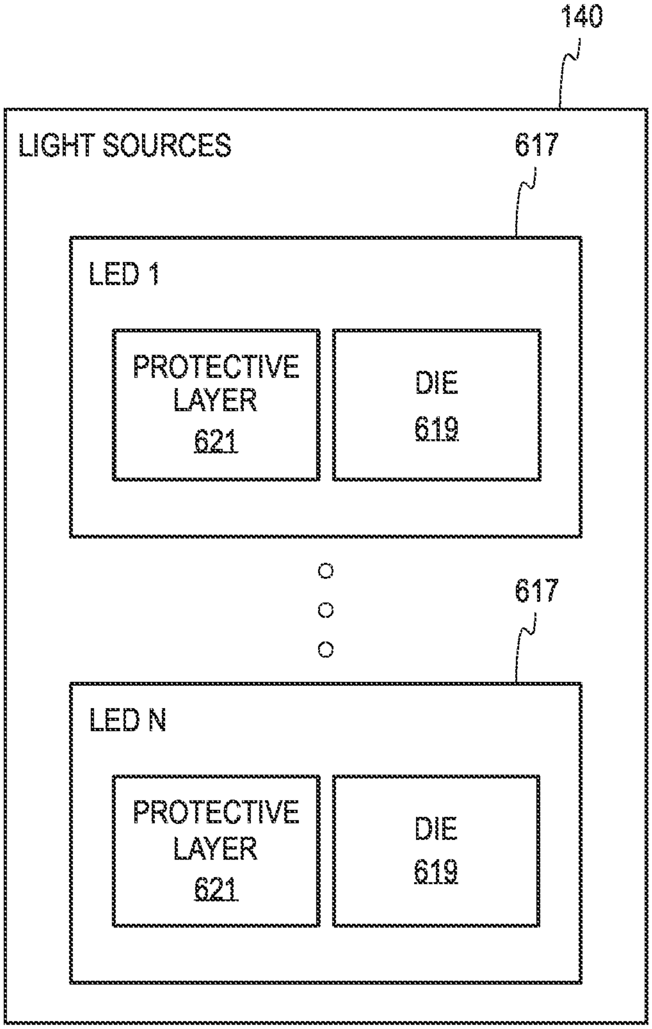
FIG. 6 depicts a simplified block diagram of a light source, according to an example.

FIG. 6 depicts a simplified block diagram of the light sources 140, according to one example. In FIGS. 4B, 5B, and 6, each light source 140 is a LED 617 that includes a die 619 and a protective layer 621. The protective layer 621 can be a layer of an optically transparent material such as, for example, a layer of silicone material. The protective layer 621 can be a non-rigid structure (e.g., a coating) in contrast to the rigid silicone lens that protect the underlying diode structure in conventional LEDs. This is possible, at least in part, because the light sources 140 are located in the cavities 415 of the optical components 301 such that the optical components 301 can protect the die 619.

By using a non-rigid protective layer 621 instead of a rigid silicone lens, the overall size of each LED 617 can be reduced. This can help to reduce a size of the optical lens assembly 142 while maintaining a ratio of an optical diameter to LED diameter. For instance, in a conventional LED, the rigid silicone lens is typically about 200% larger than a diameter of the die 619. By contrast, the LED having the non-rigid protective layer 621 described above can have a diameter of approximately 10% to approximately 50% larger than a diameter of the die 619. As one example, each LED 617 can have a diameter of approximately 1 millimeter (mm) to approximately 2 mm. Accordingly, the light source 140 described above can help to address space constraint challenges and improve light capture from light sources having a wide Lambertian optical pattern.

Figure 7A:
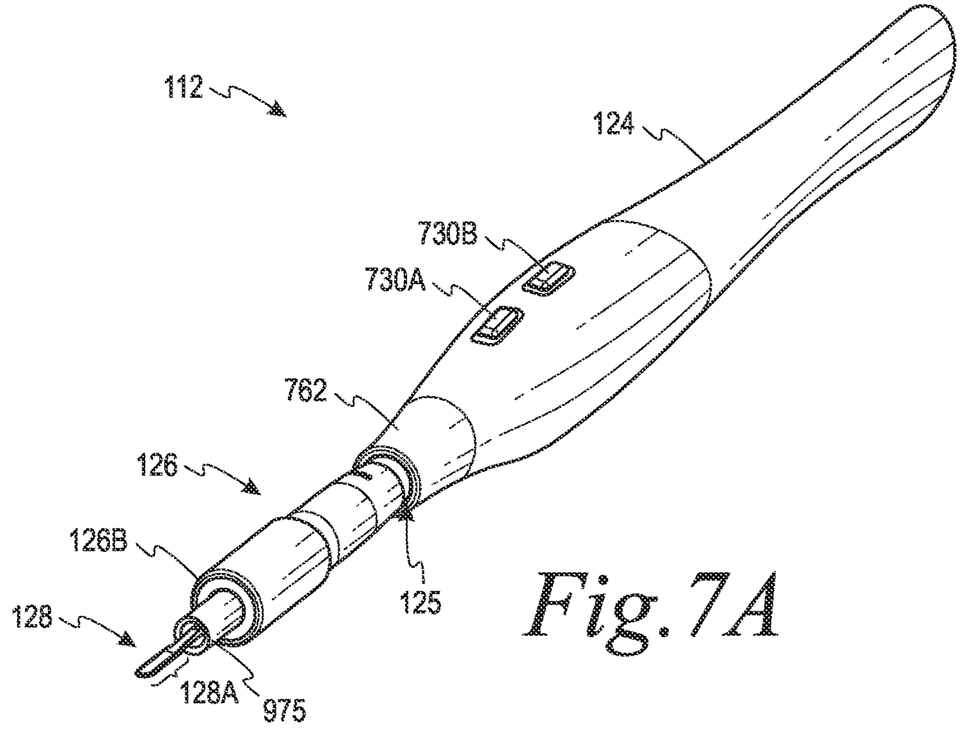
FIG. 7A depicts a perspective view of an implementation of the electrosurgical device of FIG. 1 and the optical lens assembly of FIGS. 4A-4B with a shaft in a first axial position relative to a housing, according to an example.

FIG. 7A-13 depict an implementation of the electrosurgical device 112 shown in FIG. 1 including the optical lens assembly 142 shown in FIGS. 4A-4B according to an example. As shown in FIGS. 7A-7B, the housing 123 electrosurgical device 112 includes the handle 124 having a proximal end and a distal end, and the shaft 126 extending from the distal end of the handle 124. The electrosurgical electrode 128 extends from a distal end of the shaft 126, and the plurality of light sources 140 are in the shaft 126. The handle 124 defines an interior bore 125, and the shaft 126 extends distally from the interior bore 125 of the handle 124. Also, in FIGS. 7A-7B, a distal portion 128A of the electrosurgical electrode 128 extends distally from the shaft 126. Within examples, the distal portion 128A of the electrosurgical electrode 128 can define a working end that is configured to apply electrosurgical energy to tissue.

Figure 7B:
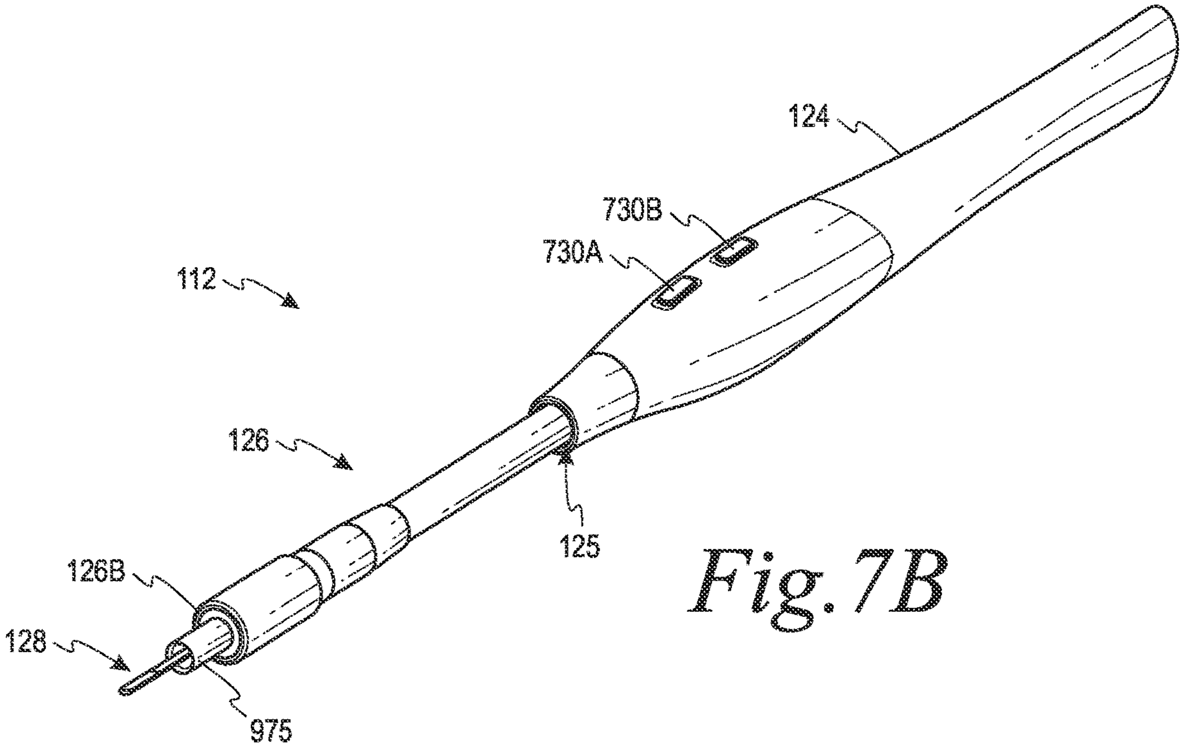
FIG. 7B depicts a perspective view of the implementation of the electrosurgical device of FIG. 7A with a shaft in a second axial position relative to the housing, according to an example.

In FIGS. 7A-7B, the shaft 126 is telescopically movable in the interior bore 125 of the handle 124 to adjust a distance of a distalmost tip of the electrosurgical electrode 128 relative to the handle 124. For instance, FIG. 7A shows the shaft 126 in a first position relative to the handle 124 along a longitudinal axis of the electrosurgical device 112, and FIG. 7B shows the shaft 126 in a second position relative to the handle 124 along the longitudinal axis of the electrosurgical device 112. In FIGS. 7A-7B, the first position is proximal of the second position such that the shaft 126 is in a retracted position in the handle 124 in the first position and the shaft 126 is in an extended position out of the handle 124 in the second position. As noted above, telescopically moving the shaft 126 relative to the handle 124 can facilitate adjusting a length of the electrosurgical device to treat differently sized and/or shaped target tissues. However, as described above, the shaft 126 can be fixedly coupled to the handle 124 such that the shaft 126 is not moveable relative to the handle 124 in other examples.

In some examples, the electrosurgical device 112 can include a collar 762 at a proximal end of the handle 124. The collar 762 can be rotatable relative to the handle 124 to increase and/or decrease friction between an outer surface of the shaft 126 and an inner surface of the collar 762. In this way, the collar 762 to allow and/or inhibit axial telescopic movement of the shaft 126 relative to the handle 124.

Additionally, in FIGS. 7A-7B, the shaft 126 is rotationally fixed relative to the handle 124, and the electrosurgical electrode 128 is rotatable relative to the handle 124 and the shaft 126. This can simplify the design and reduce a cost of manufacture of the electrosurgical device 112. For example, this arrangement of the handle 124, the shaft 126, and the electrosurgical electrode 128 can simplify electrical connections between the housing conductor 134, the shaft conductor 1236, and the electrosurgical electrode 128. Additionally, this arrangement can help to mitigate damage to the electrical connections during telescopic movement of the shaft 126 relative to the handle 124, and/or during rotation of the electrosurgical electrode 128 relative to the shaft 126 and the handle 124.

Figure 8:
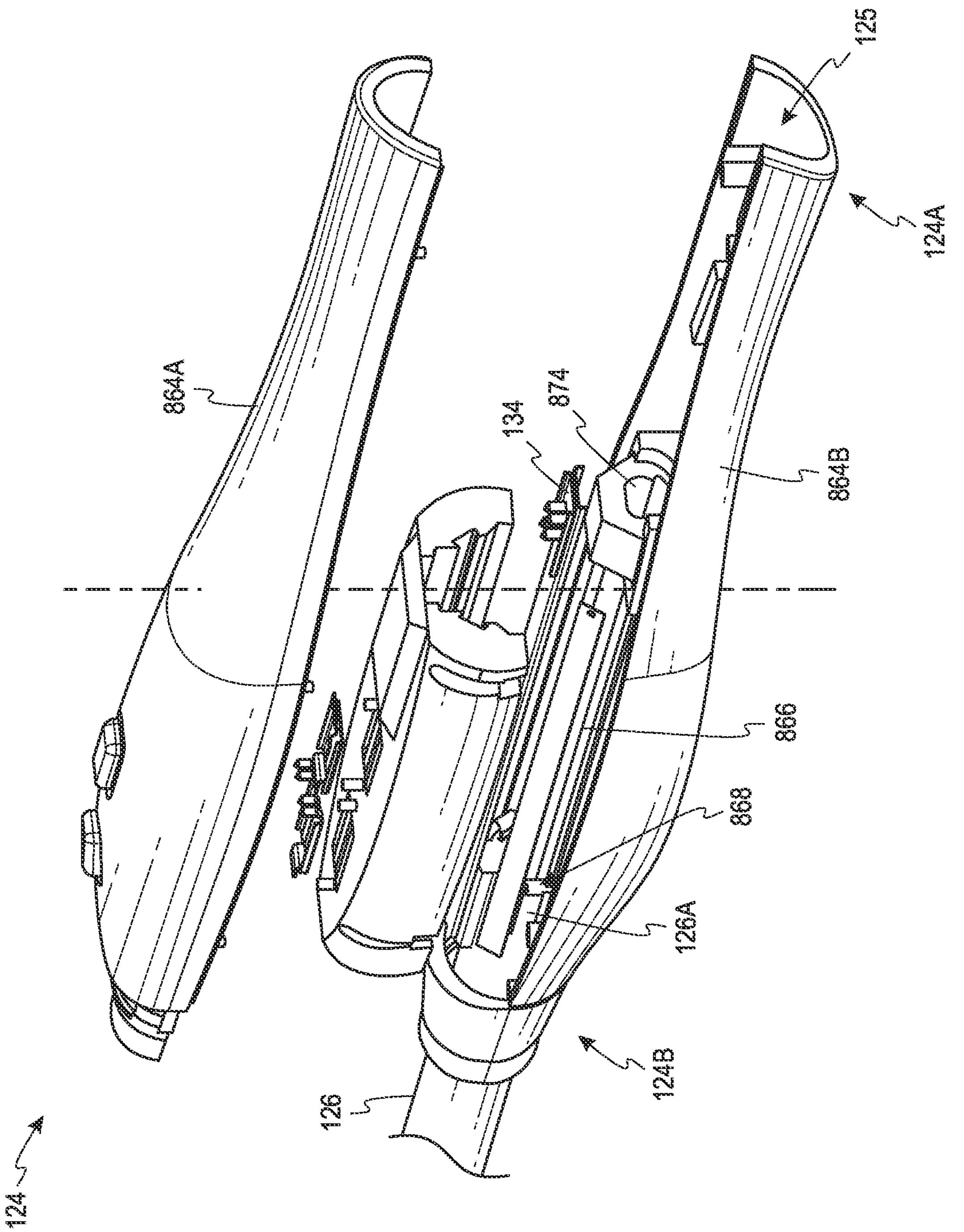
FIG. 8 depicts a partially exploded view of the housing of the electrosurgical device shown in FIGS. 7A-7B, according to an example.

FIGS. 8-13 depict additional aspects of the electrosurgical device 112 that can facilitate the telescopic and rotational movements described above. FIG. 8 depicts a partially exploded view of the handle 124. As shown in FIG. 8, the handle 124 can include a top portion 864A that can be coupled to a bottom portion 864B to define the interior bore 125 between the top portion 864A and the bottom portion 864B. In general, the interior bore 125 can be a space within the handle 124 in which one or more components of the electrosurgical device 112 can be housed.

In the interior bore 125 of the handle 124, the electrosurgical device 112 includes a shaft guide 866 that extends along a direction that is parallel to a longitudinal axis of the handle 124 (e.g., a direction extending between a proximal end 124A of the handle 124 and a distal end 124B of the handle 124). The shaft guide 866 is configured to extend in an inner cavity 868 of the shaft 126. The inner cavity 868 of the shaft 126 can be a bore that extends between a proximal end 126A of the shaft 126 to a distal end 126B of the shaft 126 (shown in FIGS. 7A-7B). As such, the inner cavity 868 can be defined by an inner surface of the shaft 126.

As shown in FIG. 8, the shaft guide 866 can have a cross-sectional shape that is non-circular to assist in preventing rotation between the shaft 126 and the handle 124. For instance, an outer surface of the shaft guide 866, which extends in the inner cavity 868 of the shaft 126, can have a non-circular shape that engages a non-circular shape of the inner surface of the shaft 126 in the inner cavity 868 of the shaft 126. In this arrangement, the shaft 126 can slide over the shaft guide 866 in a proximal direction and a distal direction (e.g., along the longitudinal axis of the handle 124), but the shaft 126 is prevented from rotating relative to the shaft guide 866 due to the engagement between (i) the inner surface of the inner cavity 868 of the shaft 126, and (ii) the outer surface of the shaft guide 866.

Also, as shown in FIG. 8, the shaft guide 866 is rotationally fixed relative to the handle 124. For instance, a portion of the shaft guide 866 can have a non-circular shape that can engage a structure in the handle 124 that has a corresponding shape. In FIG. 8, for example, a proximal portion of the shaft guide 866 has a hexagonal feature that engages a hexagonally shaped socket formed in an interior wall of the handle 124 (e.g., an interior wall of the top portion 864A and/or the bottom portion 864B of the handle 124) to prevent rotation between the shaft guide 866 and the handle 124. In this arrangement, the shaft 126 is rotationally fixed relative to the handle 124 as a result of a first non-rotational engagement between the shaft 126 and the shaft guide 866, and a second non-rotational engagement between the shaft guide 866 and the handle 124.

Figure 9:
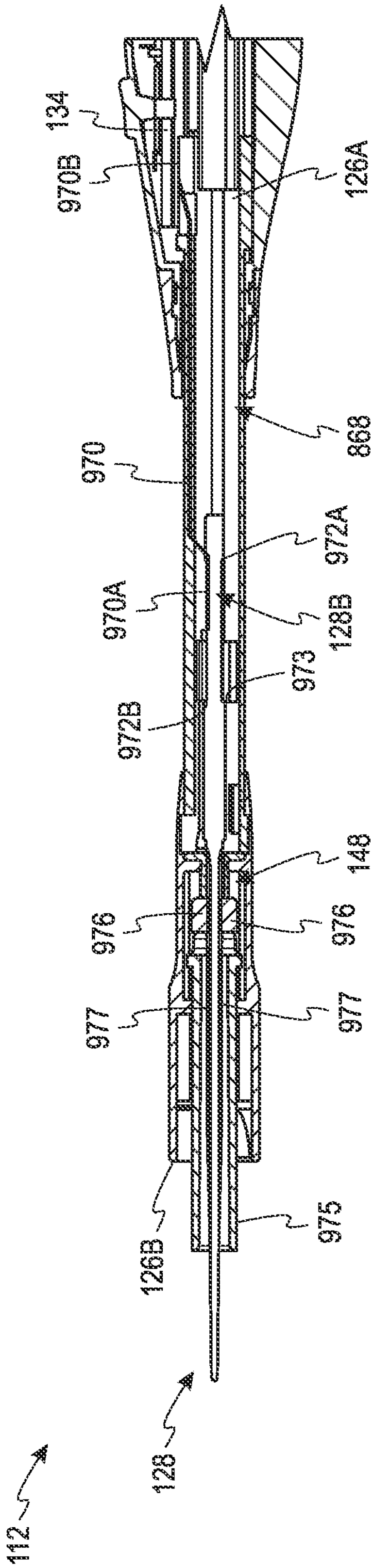
FIG. 9 depicts a cross-sectional view of a distal portion of the housing, the shaft, and an electrosurgical electrode for the example implementation shown in FIGS. 7A-7B, according to an example.
Figure 10:
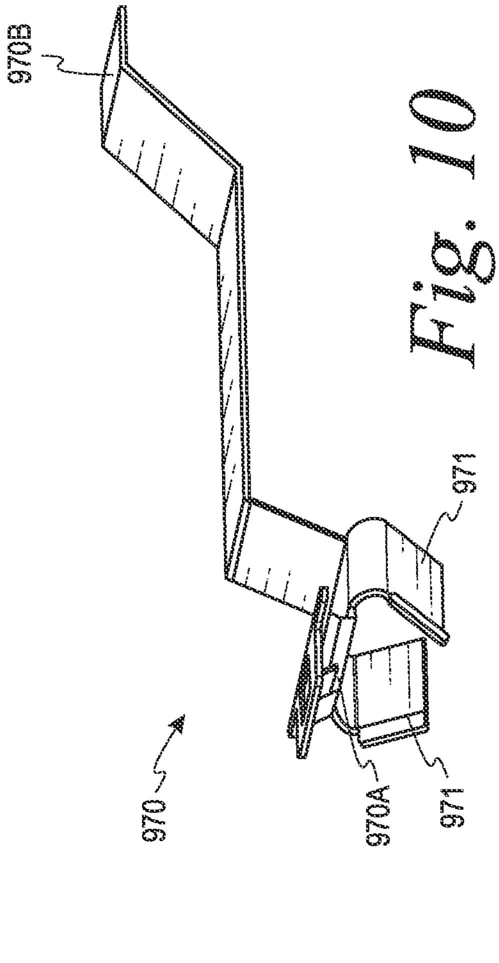
FIG. 10 depicts a perspective view of an electrical contact, according to example.

As noted above, the electrosurgical electrode 128 is coupled to the shaft 126 and the electrosurgical electrode 128 is rotatable relative to the handle 124 and the shaft 126. An example arrangement for coupling the electrosurgical electrode 128 to the shaft 126 in a manner that allows for such rotation of the electrosurgical electrode 128 is shown in FIGS. 9-10. FIG. 9 depicts a cross-sectional view of a distal portion of the handle 124, the shaft 126, and the electrosurgical electrode 128 for the example implementation shown in FIGS. 7A-7B. FIG. 9 also depicts a portion of the housing conductor 134 and an electrical contact 970 of the shaft conductor 136 according to an example. FIG. 10 depicts a perspective view of the electrical contact 970 shown in FIG. 9.

As shown in FIG. 9, the shaft 126 can include the electrical contact 970, which is coupled to a proximal portion 128B of the electrosurgical electrode 128. In particular, the electrical contact 970 is coupled to the proximal portion 128B of the electrosurgical electrode 128 such that the electrosurgical electrode 128 is rotatable relative to the electrical contact 970. In this example, the electrosurgical electrode 128 and the electrical contact 970 are electrically coupled in all rotational positions of the electrosurgical electrode 128 relative to the electrical contact 970.

In an example, the electrical contact 970 can frictionally engage the proximal portion 128B of the electrosurgical electrode 128 such that (i) the electrical contact 970 inhibits rotation of the electrosurgical electrode 128 relative to the electrical contact 970 when a force that is less than a threshold force is applied to the electrosurgical electrode 128, and (ii) the electrical contact 970 allows rotation of the electrosurgical electrode 128 relative to the electrical contact 970 when a force that is greater than the threshold force is applied to the electrosurgical electrode 128. The threshold force can be an amount of force that is great enough to prevent the electrosurgical electrode 128 from freely rotating under only a gravitational force, and/or prevent the electrosurgical electrode 128 from rotating when the electrosurgical electrode 128 is used to cut and/or coagulate tissue. The threshold force can additionally or alternatively be an amount of force that is low enough to allow a user to manually rotating the electrosurgical electrode 128 relative to the handle 124 without the use of a separate tool or instrument.

To assist with providing the frictional engagement between the proximal portion 128B of the electrosurgical electrode 128 and the electrical contact 970, the electrical contact 970 can extend around at least half of a circumference of the proximal portion 128B of the electrosurgical electrode 128. For example, in FIG. 10, the electrical contact 970 includes a pair of arms 971 that extend around more than half of the circumference of the proximal portion 128B of the electrosurgical electrode 128 and are biased inwardly to apply a force to the proximal portion 128B of the electrosurgical electrode 128. The force applied by the electrical contact 970 can thus help to control the rotation of the electrosurgical electrode 128 relative to the shaft 126 and the handle 124. Additionally, in this arrangement, the arms 971 of the electrical contact 970 can allow the electrosurgical electrode 128 to rotate by more than 360 degrees about an axis of rotation (e.g., a center axis of the electrosurgical electrode 128).

The electrical contact 970 can also assist in axially retaining the electrosurgical electrode 128 in the inner cavity 868 of the shaft 126. For instance, the proximal portion 128B of the electrosurgical electrode 128 can include a first shoulder 972A that can engage the electrical contact 970 to inhibit or prevent axial movement of the electrosurgical electrode 128 relative to the shaft 126 in the distal direction. Additionally, for instance, the proximal portion 128B of the electrosurgical electrode 128 can include a second shoulder 972B that can engage a stop 973 of the shaft 126 to inhibit axial movement of the electrosurgical electrode 128 relative to the shaft 126 in the proximal direction.

In some examples, the engagement between the first shoulder 972A and the electrical contact 970 can inhibit or prevent removal of the electrosurgical electrode 128 from the shaft 126 such that the electrosurgical electrode 128 is fixedly coupled to the shaft 126. In alternative examples, the engagement between the first shoulder 972A and the electrical contact 970 can allow for the electrosurgical electrode 128 to be removed and replaced with another electrosurgical electrode 128.

Additionally, as shown in FIGS. 9-10, the electrical contact 970 can include a first end 970A that is coupled to the proximal portion 128B of the electrosurgical electrode 128, and a second end 970B that extends into the handle 124. As shown in FIG. 9, the second end 970B engages the housing conductor 134 that extends along the handle 124 in a direction parallel to a longitudinal axis of the handle 124. In this example, the second end 970B of the electrical contact 970 is configured to remain engaged with the housing conductor 134 while the shaft 126 moves telescopically relative to the handle 124. For instance, the electrical contact 970 is fixedly coupled to the shaft 126 such that the electrical contact 970 moves with the shaft 126 relative to the handle 124. In this arrangement, the second end 970B of the electrical contact 970 can continuously engage and electrically couple to the housing conductor 134 while the second end 970B slides along the housing conductor 134 responsive to the shaft 126 moving axially relative to the handle 124. In this way, the electrical contact 970 can facilitate supplying electrosurgical energy tot the electrosurgical electrode 128 in any rotational position and/or in any axial position of the electrosurgical electrode 128 relative to the handle 124.

As shown in FIG. 9, the shaft 126 can also include the smoke evacuation channel 148 extending from a proximal end 126A of the shaft 126 to a distal end 126B of the shaft 126. For instance, in FIGS. 7A, 7B, and 9, the electrosurgical electrode 128 extends through the inner cavity 868 of the shaft 126 such that smoke evacuation channel 148 can include a gap defined between the electrosurgical electrode 128 and the inner surface of the shaft 126. In the illustrated example, the shaft 126 has a center axis that extends between the proximal end 126A and the distal end 126B, and the electrosurgical electrode 128 has a center axis that is collinear with the center axis of the shaft 126. In this arrangement, the smoke evacuation channel 148 can have a substantially constant size around a circumference of the electrosurgical electrode 128. This can help to provide relatively consistent suction each point around the electrosurgical electrode 128. However, in other examples, the center axes of the electrosurgical electrode 128 and the shaft 126 can be offset and parallel relative to each other.

Referring to FIG. 8, the inner cavity 868 at the proximal end 126A of the shaft 126 can provide a proximal end of the smoke evacuation channel 148 (shown in FIG. 9). The proximal end of the smoke evacuation channel 148 can be in fluid communication with the smoke evacuation chamber 152 of the handle 124. For instance, in FIG. 8, the smoke evacuation chamber 152 can include a bore 874 in the shaft guide 866 and a portion of the interior bore 125 of the handle 124 that is proximal of the shaft guide 866.

Referring again to FIG. 9, the electrosurgical device 112 can also include a suction sleeve 975 that can be fluidly coupled to the smoke evacuation channel 148 in the shaft 126. As shown in FIG. 9, a distal portion of the suction sleeve 975 can extend distally from the distal end 126B of the shaft 126, and the electrosurgical electrode 128 can extend through the suction sleeve 975. In particular, the suction sleeve 975 can be spaced apart from the electrosurgical electrode 128 to define a smoke inlet that can extend circumferentially around the center axis of the distal portion 128A of the electrosurgical electrode 128.

In an example, the suction sleeve 975 can be rotationally fixed relative to the electrosurgical electrode 128 such that rotation of the suction sleeve 975 relative to the shaft 126 causes a corresponding rotation of the electrosurgical electrode 128 relative to the shaft 126 and the handle 124. In this arrangement, the user can use the suction sleeve 975 to rotate the electrosurgical electrode 128 relative to the handle 124. This can beneficially allow the user to avoid directly touching the electrosurgical electrode 128 as the electrosurgical electrode 128 may be at relatively elevated temperatures after or during use. Additionally, because directly touching the electrosurgical electrode 128 may negatively impact a coating on the electrosurgical electrode 128, the suction sleeve 975 can help to maintain the structural integrity and operational performance of the electrosurgical electrode 128.

In FIG. 9, the suction sleeve 975 includes one or more teeth 976, and the electrosurgical electrode 128 includes one or more slots 977. Each of the one or more teeth 976 of the suction sleeve 975 are in a respective one of the one or more slots 977 such that the one or more teeth 976 engage the one or more slots 977 to cause the electrosurgical electrode 128 to rotate responsive to rotation of the suction sleeve 975. However, in another example, the suction sleeve 975 can include the one or more slots 977 and the electrosurgical electrode 128 can include the one or more teeth 976.

In some examples, the suction sleeve 975 can be telescopically moveable in the inner cavity 868 of the shaft 126 to adjust a distance between the suction sleeve 975 and a distalmost tip of the electrosurgical electrode 128. For instance, each of the one or more teeth 976 can be configured to slide longitudinally in the respective one of the one or more slots 977 responsive to the suction sleeve 975 telescopically moving relative to the shaft 126 and/or the electrosurgical electrode 128. In this telescoping arrangement, the suction sleeve 975 can move relative to the shaft 126 and the electrosurgical electrode 128 to adjust an extent of the distal portion 128A of the electrosurgical electrode 128 that is exposed. Specifically, the suction sleeve 975 can be (i) moved toward the distal end 126B of the shaft 126 to expose a greater extent of the electrosurgical electrode 128 and improve visibility at the surgical site, and (ii) moved away from the distal end 126B of the shaft 126 to expose a lesser extent of the electrosurgical electrode 128 and capture relatively greater amounts of smoke at the surgical site.

Although it can be beneficial for the suction sleeve 975 to be telescopically movable relative to the shaft 126 and/or the electrosurgical electrode 128, the suction sleeve 975 can be axially fixed relative to the shaft 126 and/or the electrosurgical electrode 128 in other examples. This can simplify manufacturing and reduce a cost of manufacture.

In one example, the suction sleeve 975 can be substantially transparent such that the electrosurgical electrode 128 is visible through the suction sleeve 975. This can help to help improve visibility of the electrosurgical electrode 128. However, in other examples, the suction sleeve 975 can be made from an opaque material.

Figure 11:
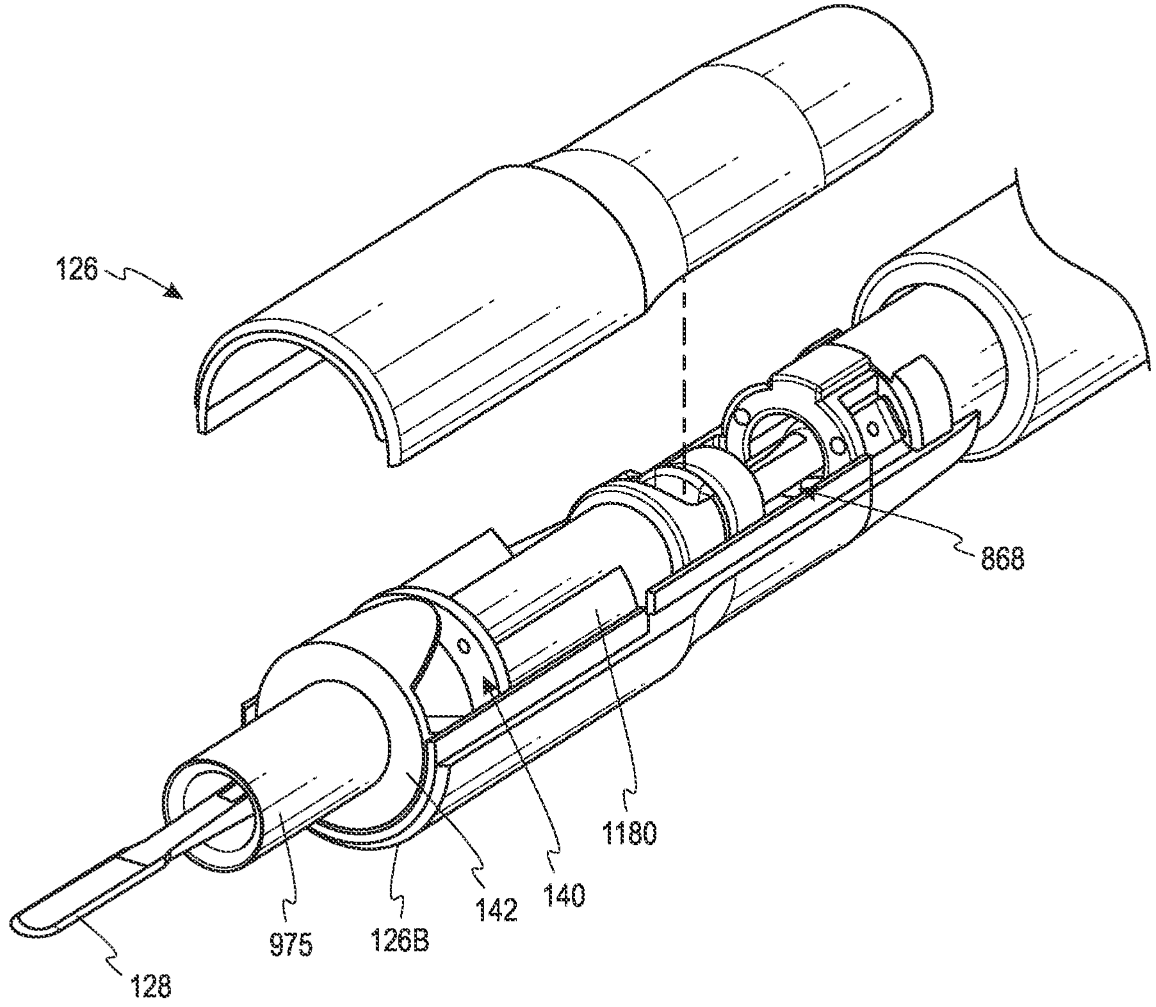
FIG. 11 depicts a distal portion of the shaft with a top portion removed to show optical components located in an inner cavity of the shaft for the example implementation shown in FIGS. 7A-7B, according to an example.
Figure 12:
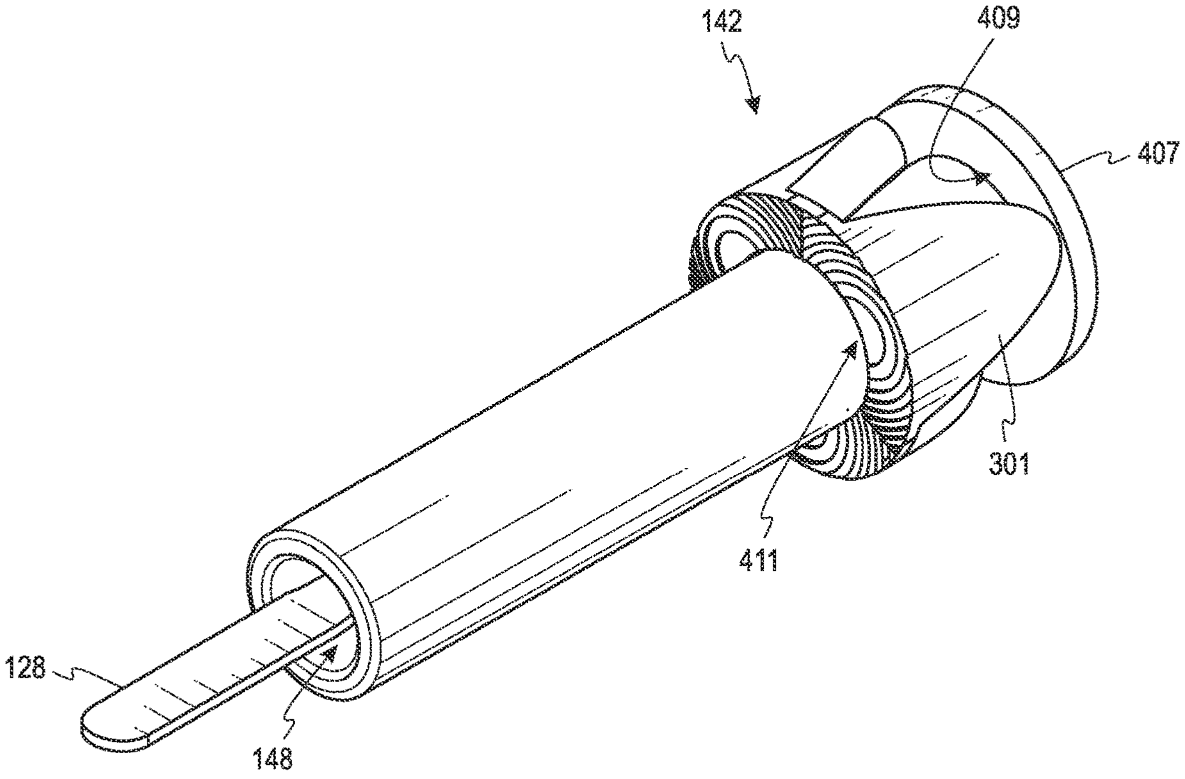
FIG. 12 depicts an assembly of an electrosurgical electrode, a suction sleeve, the optical lens assembly of FIGS. 4A-4B, and a light source, according to an example.

FIG. 11 depicts a distal portion of the shaft 126 with a top portion removed to show optical components located in the inner cavity 868 of the shaft 126. FIG. 12 depicts the optical lens assembly 142 shown in FIGS. 4A-4B with the electrosurgical electrode 128 and the suction sleeve 975 that defines a portion of the smoke evacuation channel 148 extending through the lens aperture 411 of the optical lens assembly 142 and the PCB aperture 409 of the LED PCB 407.

As shown in FIGS. 9 and 11-12, the electrosurgical device 112 can include the light sources 140 and the optical lens assembly 142 in the inner cavity 868 of the shaft 126. As noted above, the light sources 140 are configured to emit light into the optical lens assembly 142, and the optical lens assembly 142 is configured to transmit the light from the light sources 140 in a distal direction and emit the light from the distal end 126B of the shaft 126.

As shown in FIG. 12, the electrosurgical electrode 128 and the suction sleeve 975 can extend through the PCB aperture 409 of the LED PCB 407 and the through-bore defined by the lens aperture 411 in the optical lens assembly 142. Additionally, as shown in FIG. 12, the light sources 140 can be located around a circumference of the electrosurgical electrode 128. In this arrangement, the electrosurgical device 112 can provide illumination and suction around the circumference of the electrosurgical electrode 128. Further, integrating the optical lens assembly 142 of FIGS. 3-4B in this arrangement can improve a quality of illumination, reduce a size of the distal end of the electrosurgical device, and improve a line of sight to the surgical site.

As shown in FIG. 11, the electrosurgical device 112 can also include a heat sink 1180 coupled a proximal side of the light source 140. This can help to reduce a temperature of the light source 140 and, thus, the electrosurgical device 112.

In an example, the light source 140, the optical lens assembly 142, and/or the heat sink 1180 can be fixedly coupled to the shaft 126. In this arrangement, the electrosurgical electrode 128 and the suction sleeve 975 can be rotatable relative to the light source 140, the optical lens assembly 142, and/or the heat sink 1180. For instance, the apertures in the light source 140, the optical lens assembly 142, and/or the heat sink 1180 can have a size and/or a shape (e.g., a circle shape) that allows the electrosurgical electrode 128 and the suction sleeve 975 to rotate in the apertures. Additionally, in this arrangement, the light source 140, the optical lens assembly 142, and the heat sink 1180 can be telescopically movable together with the shaft 126 relative to the handle 124.

Figure 13:
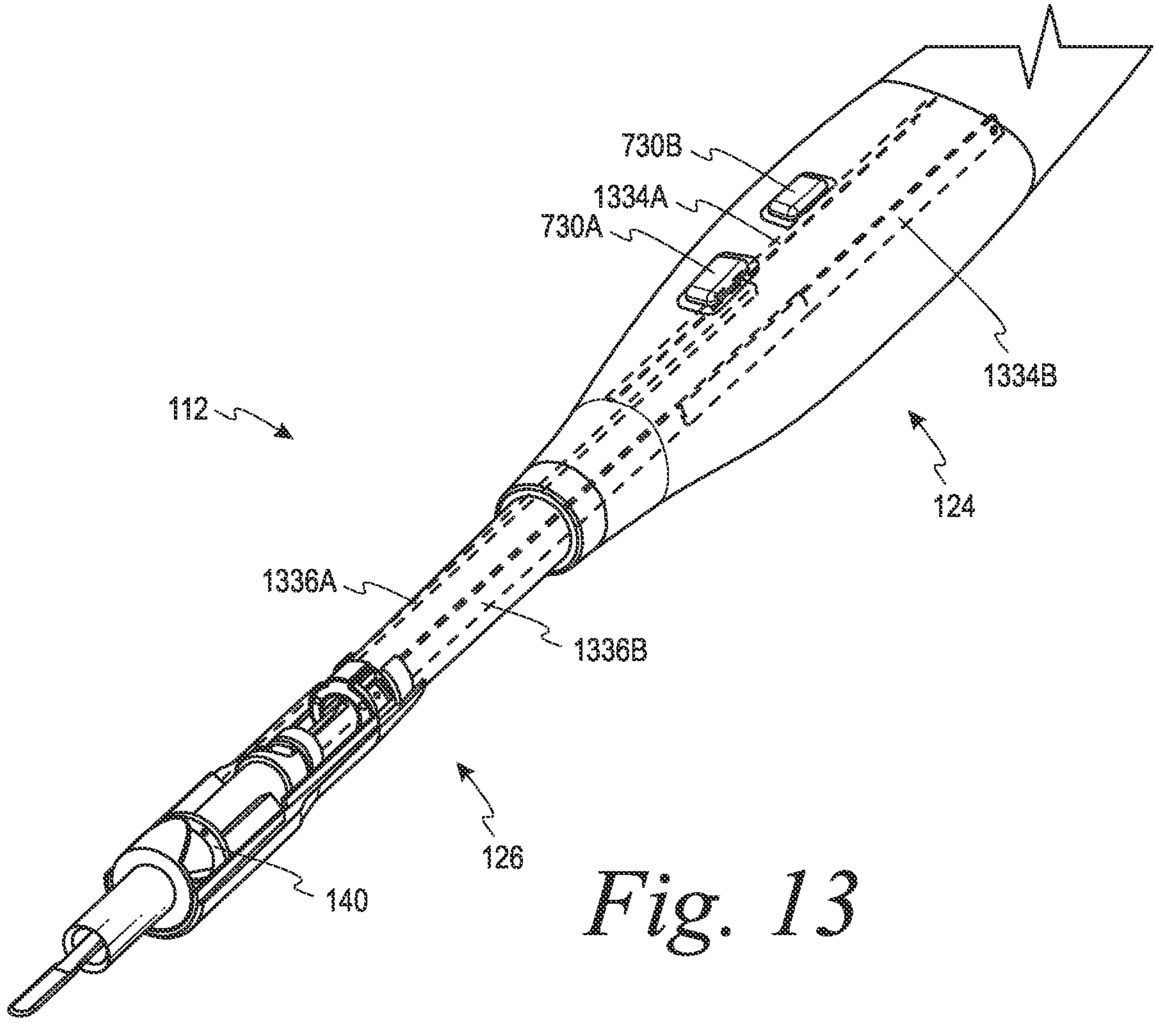
FIG. 13 depicts the electrosurgical device of FIGS. 7A-12 with components removed to show the conductors for supplying the power to a light source, according to an example.

As noted above, the housing conductor 134 and the shaft conductor 136 can provide for electrically coupling the light source 140 to the DC power source 144. FIG. 13 depicts the electrosurgical device 112 of FIGS. 7A-12 with components removed to show the housing conductors 134 and the shaft conductors 136 for supplying the DC power to the light source 140 according to an example. As shown in FIG. 13, the shaft 126 can include a positive-light electrical conductor 1336A and a negative-light electrical conductor 1336B that slidably engage corresponding electrical conductors 1334A, 1334B in the handle 124 while the shaft 126 telescopically moves in an axial direction relative to the handle 124.

As shown in FIGS. 7A-8 and 13, the user input device(s) 130 include a first button 730A and a second button 730B on an exterior surface of the handle 124. In one implementation, the first button 730A can be actuated to operate the electrosurgical device 112 in a cutting mode of operation, and the second button 730B can be actuated to operate the electrosurgical device 112 in a coagulation mode of operation. In this example, a third button (not shown) can be provided on the plug of the power cord 122 and/or on the electrosurgical generator 110, and the third button can be actuated to operate the light source 140 (i.e., to cause the light source 140 to emit light or cease emitting light). As described above, the user input device(s) 130 can be configured differently in other examples. For instance, the electrosurgical device 112 can be operable in a lesser quantity of modes of operation, a greater quantity of modes of operation, and/or different types of modes of operation in other examples (e.g., such as the example modes of operation described above). Additionally, for instance, the at least one user input device 130 can additionally or alternatively include the user interface 116 of the electrosurgical generator 110 and/or another external device (e.g., a footswitch) for operating the electrosurgical device 112 in one or more modes of operation. Also, for instance, the user input devices 130 on the handle 124 can include the third button for operating the light source 140.

Figure 14:
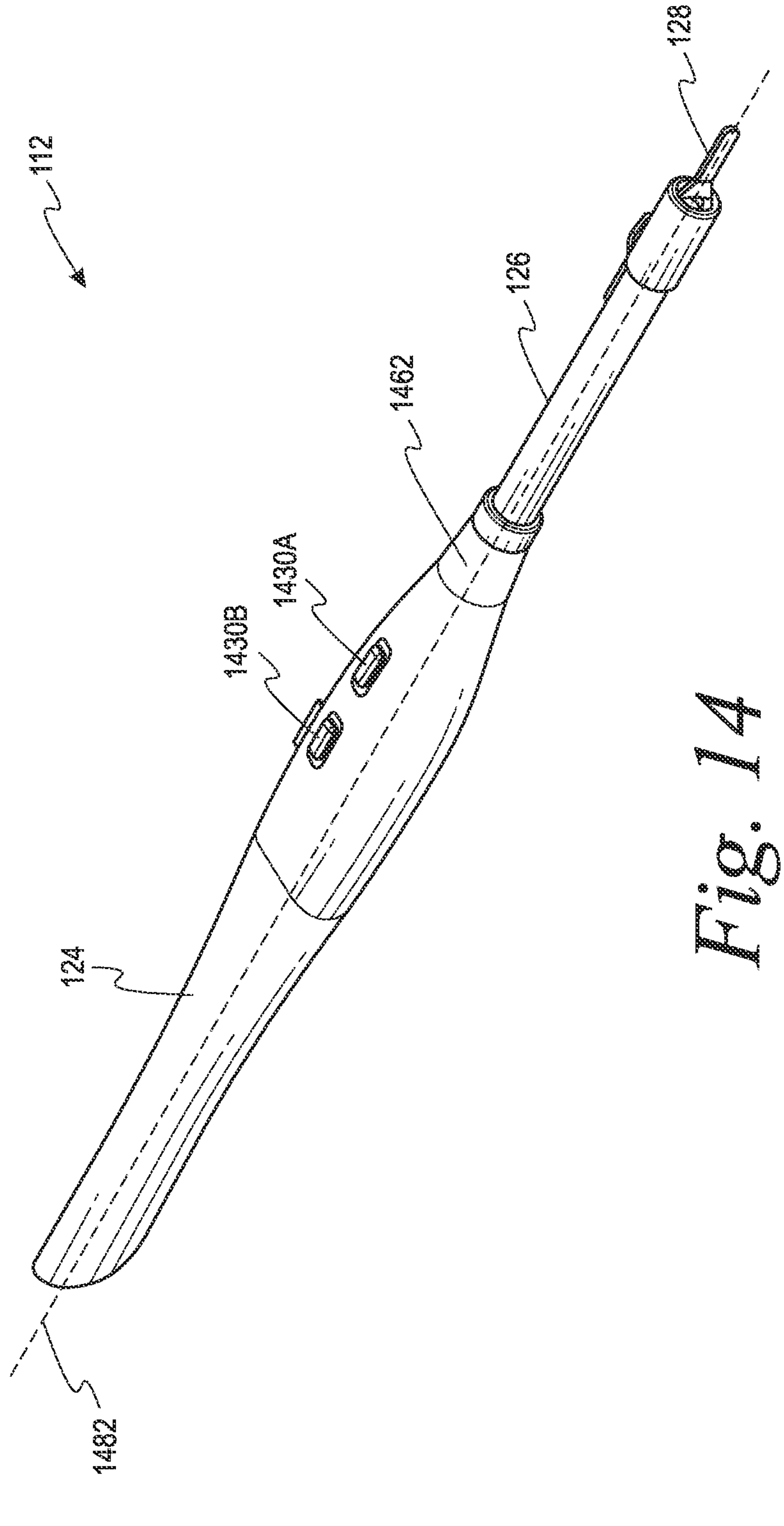
FIG. 14 depicts a perspective view of another implementation of the electrosurgical device of FIG. 1 and the optical lens assembly of FIGS. 5A-5B, according to another example.
Figure 15:
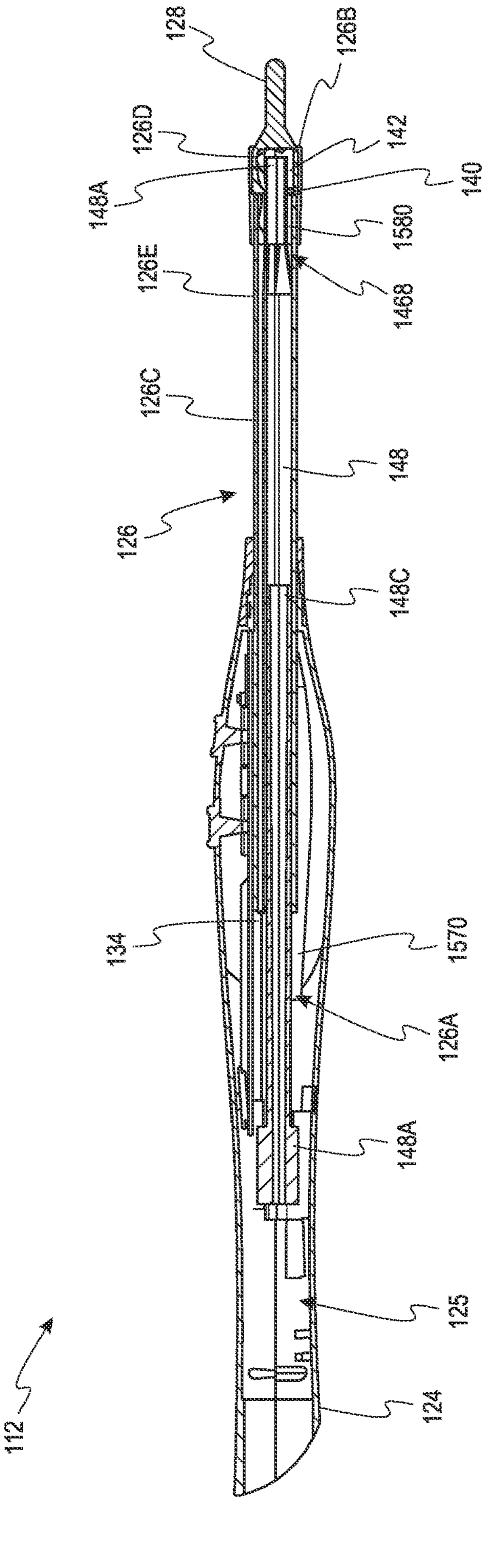
FIG. 15 depicts a cross-sectional view of the electrosurgical device shown in FIG. 14 taken through a longitudinal axis of the electrosurgical device, according to the example.

FIGS. 14-20 depict an implementation of the electrosurgical device 112 of FIG. 1 and the optical lens assembly 142 of FIGS. 5A-5B according to another example. FIG. 14 depicts a perspective view of the electrosurgical device 112 according to the example. FIG. 15 depicts a cross-sectional view of the electrosurgical device 112 taken through a longitudinal axis 1482 of the electrosurgical device according to the example.

As shown in FIGS. 14-15, the electrosurgical device 112 includes the handle 124 defining an interior bore 125, the shaft 126 extending distally from the interior bore 125 of the handle 124, and a smoke evacuation channel 148 in the inner cavity 1468 of the shaft 126. The shaft 126 has a longitudinal axis 1482 extending between a proximal end 126A of the shaft 126 and a distal end 126B of the shaft 126. Additionally, the electrosurgical electrode 128 extends distally from a distal end 126B of the shaft 126.

In an example, the shaft 126 can be telescopically movable in the interior bore 125 of the handle 124 to adjust a distance of a distalmost tip of the electrosurgical electrode 128 relative to the handle 124. As noted above, telescopically moving the shaft 126 relative to the handle 124 can facilitate adjusting a length of the electrosurgical device to treat differently sized and/or shaped target tissues. However, as described above, the shaft 126 can be fixedly coupled to the handle 124 such that the shaft 126 is not moveable relative to the handle 124 in other examples.

In some examples, the electrosurgical device 112 can include a collar 1462 at a proximal end of the handle 124. The collar 1462 can be rotatable relative to the handle 124 to increase and/or decrease friction between an outer surface of the shaft 126 and an inner surface of the collar 1462. In this way, the collar 1462 to allow and/or inhibit axial telescopic movement of the shaft 126 relative to the handle 124.

Additionally, in FIGS. 14-15, the shaft 126 is rotatable relative to the handle 124, and the smoke evacuation channel 148 is rotationally fixed relative to the handle 124. Additionally, as described in further detail below, the electrosurgical device 112 can further include the light sources 140 and the optical lens assembly 142 of FIGS. 5A-5B, which can both be rotationally fixed relative to the handle 124. Providing for rotation of the electrosurgical electrode 128 together with the shaft 126 while rotationally fixing the smoke evacuation 148, the light sources 140, and/or the optical lens assembly 142 can help to simplify the design and/or reduce a cost of manufacture for the electrosurgical device 112.

The rotational arrangement of these components of the electrosurgical device 112 can be achieved, at least in part, as a result of the electrosurgical electrode 128 extending distally from the distal end 126B of the shaft 126 such that (i) the shaft 126 conducts electrosurgical energy to the electrosurgical electrode 128, and (ii) rotation of the shaft 126 relative to the handle 124 causes corresponding rotation of the electrosurgical electrode 128 relative to the handle 124. For example, at least a portion of the shaft 126 can be formed of an electrically conductive material such that the shaft 126 is the shaft conductor 136 (e.g., a conductive tube at least partially defining the inner cavity 1468) for supplying the electrosurgical energy to the electrosurgical electrode 128.

In one example, the electrosurgical electrode 128 and the shaft 126 are formed as a single-part, monolithic structure. This can be beneficial in an implementation in which the electrosurgical electrode 128 is permanently fixed to the shaft 126 such that the electrosurgical electrode 128 cannot be replaced with another electrosurgical electrode 128. In another example, the electrosurgical electrode 128 and the shaft 126 can be separate components that are coupled to each other (e.g., by welding, soldering, and/or a friction fit coupling). In some implementations in which the electrosurgical electrode 128 and the shaft 126 are separate components, the electrosurgical electrode 128 can be removable from the shaft 126 and replaced with another electrosurgical electrode 128. In other implementations, the electrosurgical electrode 128 can be permanently fixed to the shaft 126 such that the electrosurgical electrode 128 cannot be replaced with another electrosurgical electrode 128.

In FIGS. 14-15, the shaft 126 includes an electrically conductive portion 126C and an insulator portion 126D. As noted above, the electrosurgical electrode 128 can extend from the electrically conductive portion 126C of the shaft 126. The insulator portion 126D of the shaft 126 can be a sleeve structure that covers an interface between the electrosurgical electrode 128 and the electrically conductive portion 126C of the shaft 126. In this arrangement, the insulator portion 126D can help to mitigate arcing and/or help to supply the electrosurgical energy to the electrosurgical electrode 128. Additionally, the shaft 126 can include a layer of insulator material 126E (e.g., a heat shrink material) covering a remainder of the electrically conductive portion 126C of the shaft 126 (e.g., a portion that is not covered by the insulator portion 126D of the shaft 126) to mitigate arcing and/or help to supply the electrosurgical energy to the electrosurgical electrode 128.

Figure 16:
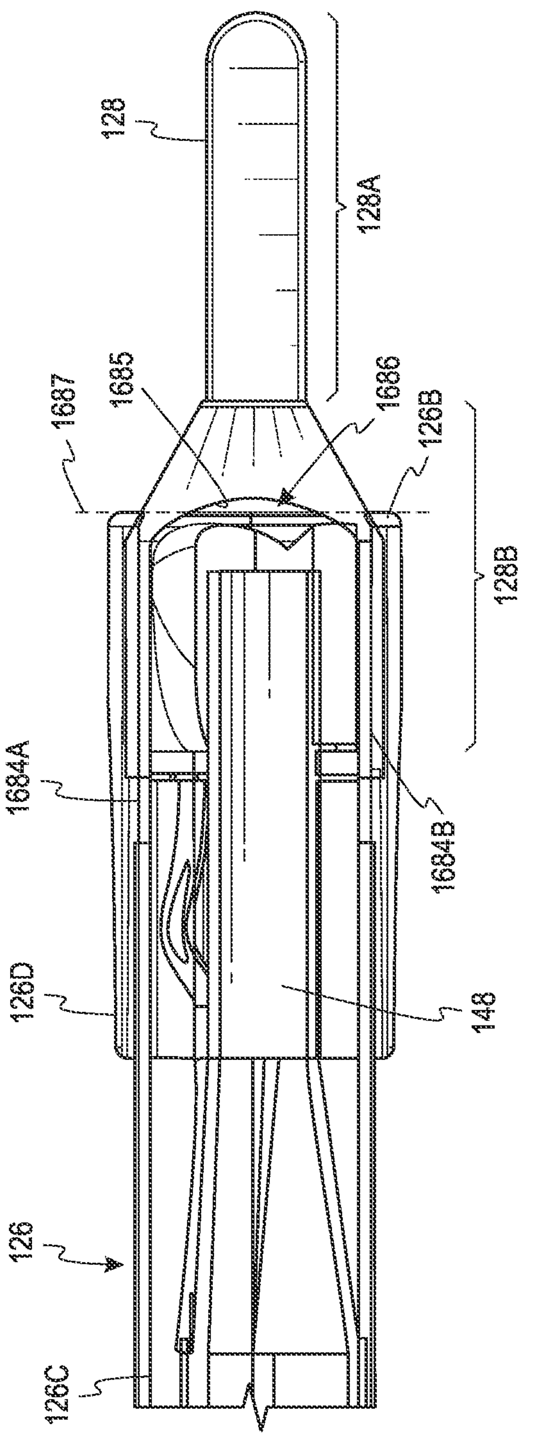
FIG. 16 depicts an enlarged view of the cross-section of a distal end of a shaft and an electrosurgical electrode shown in FIG. 15, according to an example.

Referring now to FIG. 16, an enlarged view of the cross-section of the distal end 126B of the shaft 126 and the electrosurgical electrode 128 taken through the longitudinal axis 1482 is shown according to an example. As shown in FIG. 16, a distal portion 128A of the electrosurgical electrode 128 can define a working end that is configured to apply electrosurgical energy to tissue. A proximal portion 128B of the electrosurgical electrode 128 can include a first leg 1684A extending from a distal end 126B of the shaft 126, and a second leg 1684B extending from the distal end of the conductive portion 126C of the shaft 126.

In FIG. 16, the first leg 1684A and the second leg 1684B are diametrically opposed to each other around a circumference of the distal end 126B of the shaft 126. Additionally, a proximal-facing surface 1685 of the proximal portion 128B of the electrosurgical electrode 128 can taper, along a distal direction, toward a center axis of the shaft 126 to define a gap 1686 between the proximal-facing surface 1685 and a plane 1687 at a distalmost end of the shaft 126. The gap 1686 can help to improve air flow and suction at the distal end 126B of the shaft 126.

Additionally, as shown in FIG. 16, the sleeve structure of the insulator portion 126D can extend around the optical lens assembly 142. The sleeve structure may be an optically opaque material. To enhance an intensity of the light emitted from the optical lens assembly 142, at least a portion of each distal transmission surface the optical lens assembly 142 can extend to a position distal of a distal-most end of the sleeve structure of the insulator portion 126D.

Referring back to FIG. 15, the shaft 126 can include an electrical contact 1570 that engages the housing conductor 134 that extends along the handle 124 in a direction parallel to a longitudinal axis 1482 (as shown in FIG. 14) of the handle 124. The electrical contact 1570 can be configured to remain engaged with the housing conductor 134 while the shaft 126 moves telescopically relative to the handle 124. For instance, the electrical contact 1570 is fixedly coupled to the shaft 126 such that the electrical contact 1570 moves with the shaft 126 relative to the handle 124. In this arrangement, the electrical contact 1570 can continuously engage and electrically couple to the housing conductor 134 while the electrical contact 1570 slides along the housing conductor 134 responsive to the shaft 126 moving axially relative to the handle 124.

Additionally, the electrical contact 1570 can extend around a circumference of the shaft 126 such that the electrical contact 1570 can remain engaged with the housing conductor 134 in all rotational positions of the shaft 126 and the electrosurgical electrode 128 relative to the handle 124. In this way, the electrical contact 1570 can facilitate supplying electrosurgical energy tot the electrosurgical electrode 128 in any rotational position and/or in any axial position of the electrosurgical electrode 128 relative to the handle 124.

In one example, the shaft 126 and the electrosurgical electrode 128 can be rotatable by more than 360 degrees relative to the handle 124. In this example, the electrical contact 1570 can extend entirely around the circumference of the shaft 126. In another example, the shaft 126 and the electrosurgical electrode 128 can be rotatable by less than 360 degrees relative to the handle 124. In such an example, the electrical contact 1570 can extend around at least a portion of the circumference of the shaft 126 that is sufficient to maintain the electrical coupling between the shaft 126 and the housing conductor 134 over the entire range of rotational positions that the shaft 126 and the electrosurgical electrode 128 can be in relative to the handle 124.

As noted above, the electrosurgical electrode 128 can include a proximal portion 128B extending from the distal end of the shaft 126, and a distal portion 128A that comprises a working end configured to apply electrosurgical energy to tissue. In FIGS. 14-16, a center axis of the distal portion 128A of the electrosurgical electrode 128 and a center axis of the smoke evacuation channel 148 are collinear. In this arrangement, the smoke evacuation channel 148 can have a substantially constant size around a circumference of the electrosurgical electrode 128. This can help to provide relatively consistent suction each point around the electrosurgical electrode 128. However, in other examples, the center axes of the electrosurgical electrode 128 and the shaft 126 can be offset and parallel relative to each other.

Additionally, as shown in FIGS. 14-16, the smoke evacuation channel 148 can define a space that is void of any other structure between a proximal end 148A of the smoke evacuation channel 148 and a distal end 148B of the smoke evacuation channel 148. This can provide for more efficiently using the relatively limited size of the inner cavity 1468 to enhance suction via the smoke evacuation channel 148 as compared to other implementations in which the electrosurgical electrode 128 and/or other components are disposed in the smoke evacuation channel 148.

Figure 17:
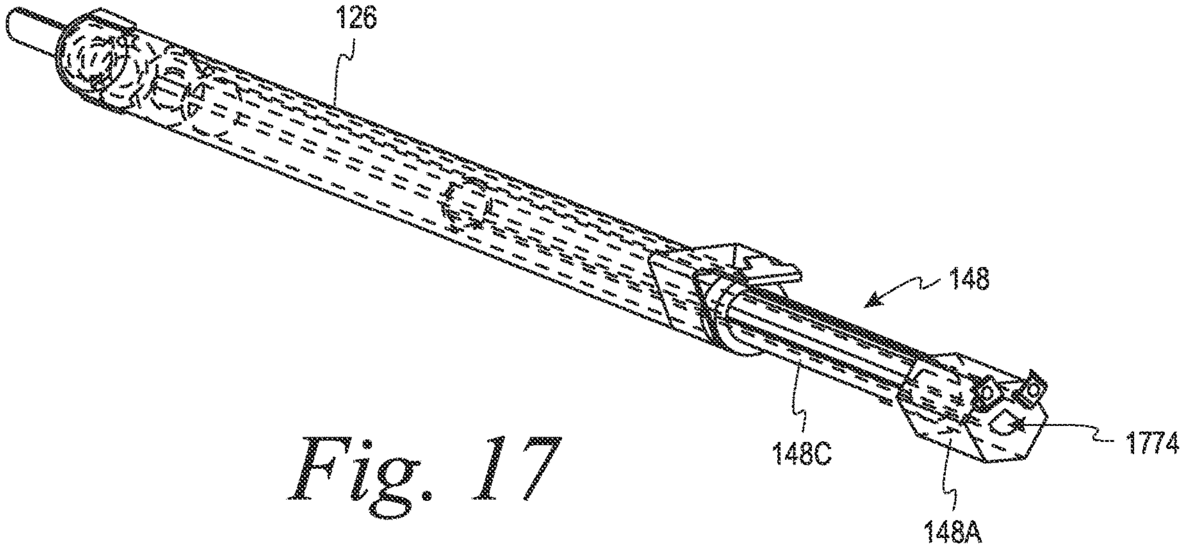
FIG. 17 depicts a perspective view of a smoke evacuation channel and a shaft of the electrosurgical device shown in FIGS. 14-16, according to an example.
Figure 18:
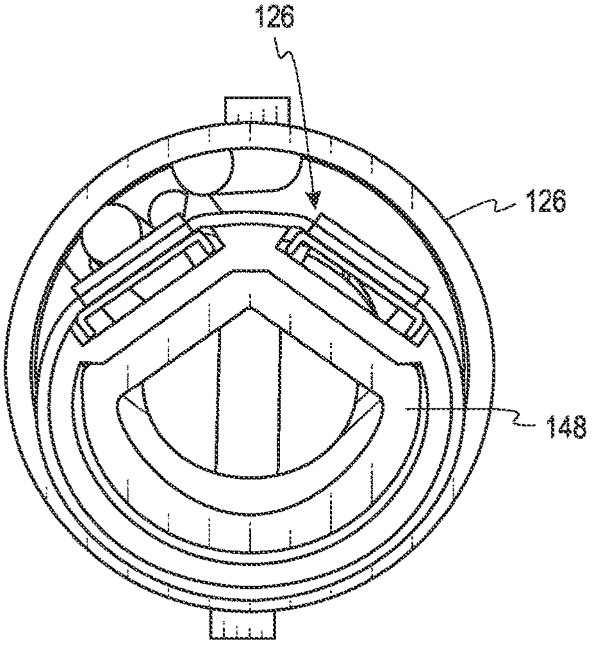
FIG. 18 depicts a side view of the smoke evacuation channel and the shaft of the electrosurgical device shown in FIGS. 14-16, according to an example.

Additionally, as noted above, the smoke evacuation channel 148 can be rotationally fixed relative to the handle 124 such that the shaft 126 and the electrosurgical electrode 128 are rotatable relative to the smoke evacuation channel 148. FIGS. 17-18 depict the smoke evacuation channel 148 and the shaft 126 according to an example. As shown in FIGS. 15 and 17-18, at least a portion of the smoke evacuation channel 148 can have a non-circular shape to inhibit rotation of the smoke evacuation channel 148 relative to the handle 124 while the shaft 126 and the electrosurgical electrode 128 rotate relative to the handle 124.

For example, the proximal end 148A of the smoke evacuation channel 148 can include a non-rotational fitting that is configured to engage with a correspondingly shaped structure in the handle 124, and the non-rotational fitting can have a non-circular cross-sectional shape. In FIGS. 15 and 17, for example, the proximal end 148A of the smoke evacuation channel 148 has a hexagonal feature that engages a hexagonally shaped socket formed in an interior wall of the handle 124 to prevent rotation between the smoke evacuation channel 148 and the handle 124. Additionally, as shown in FIG. 18, a gap can be defined between the shaft 126 and the smoke evacuation channel 148 to provide for rotation of the shaft 126 relative to the smoke evacuation channel 148.

As shown in FIG. 17, the non-rotational fitting at the proximal end 148A of the smoke evacuation channel 148 can include a through-bore 1774 that has a cross-sectional area that is less than a cross-sectional area of a body 148C of the smoke evacuation channel 148, which is proximal of the non-rotational fitting. The relatively smaller size of the through-bore 1774 can assist in directing the smoke into a relatively smaller volume of space as the smoke exits the proximal end 148A of the smoke evacuation channel 148. This can beneficially help to reduce or prevent exposing electrical components in the interior bore 125 of the handle 124 to the smoke.

Figure 19:
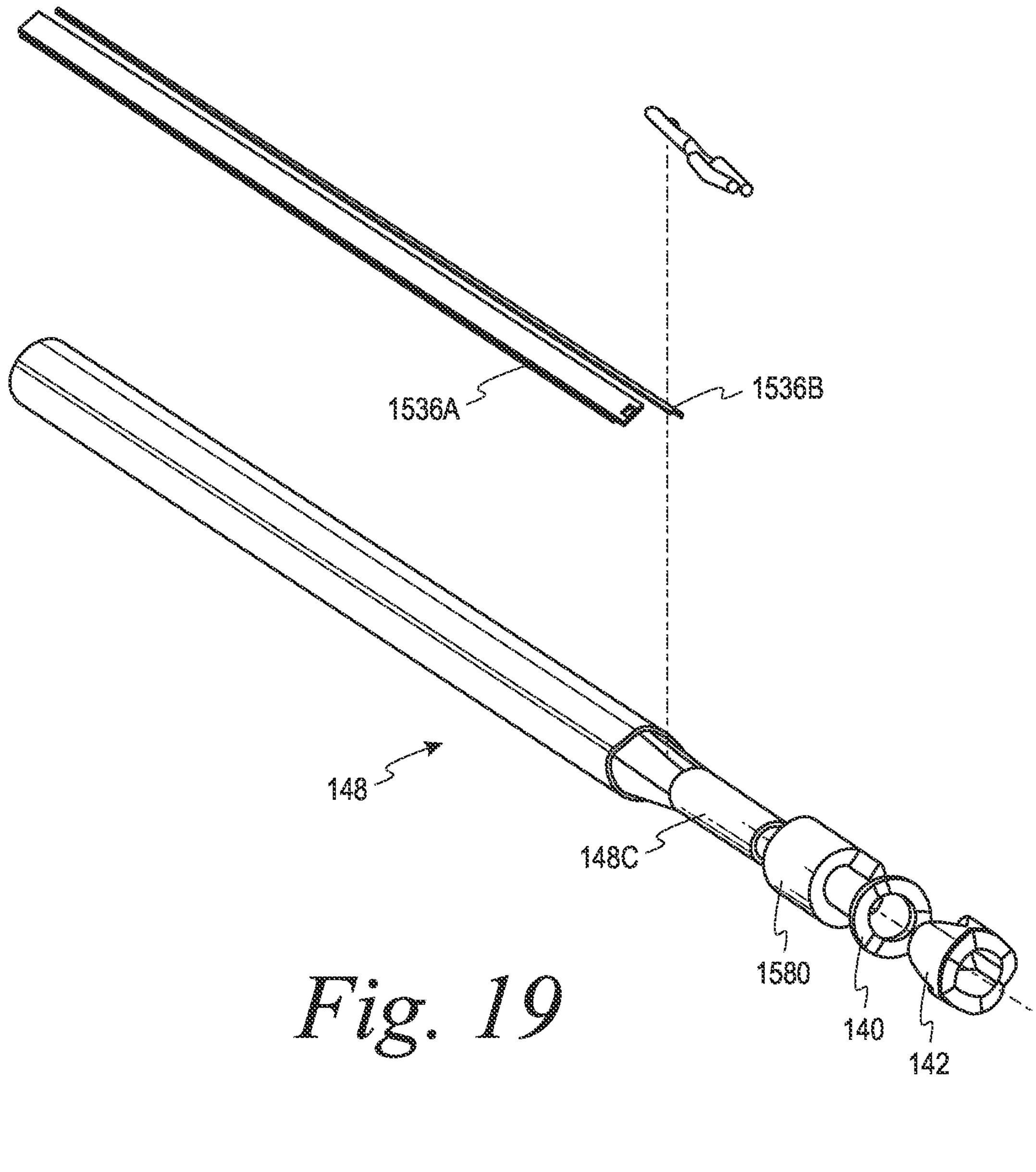
FIG. 19 depicts a partially exploded view of an assembly of a light source, an optical lens, and a heat sink on the smoke evacuation channel of the electrosurgical device shown in FIGS. 14-16, according to an example.
Figure 20:
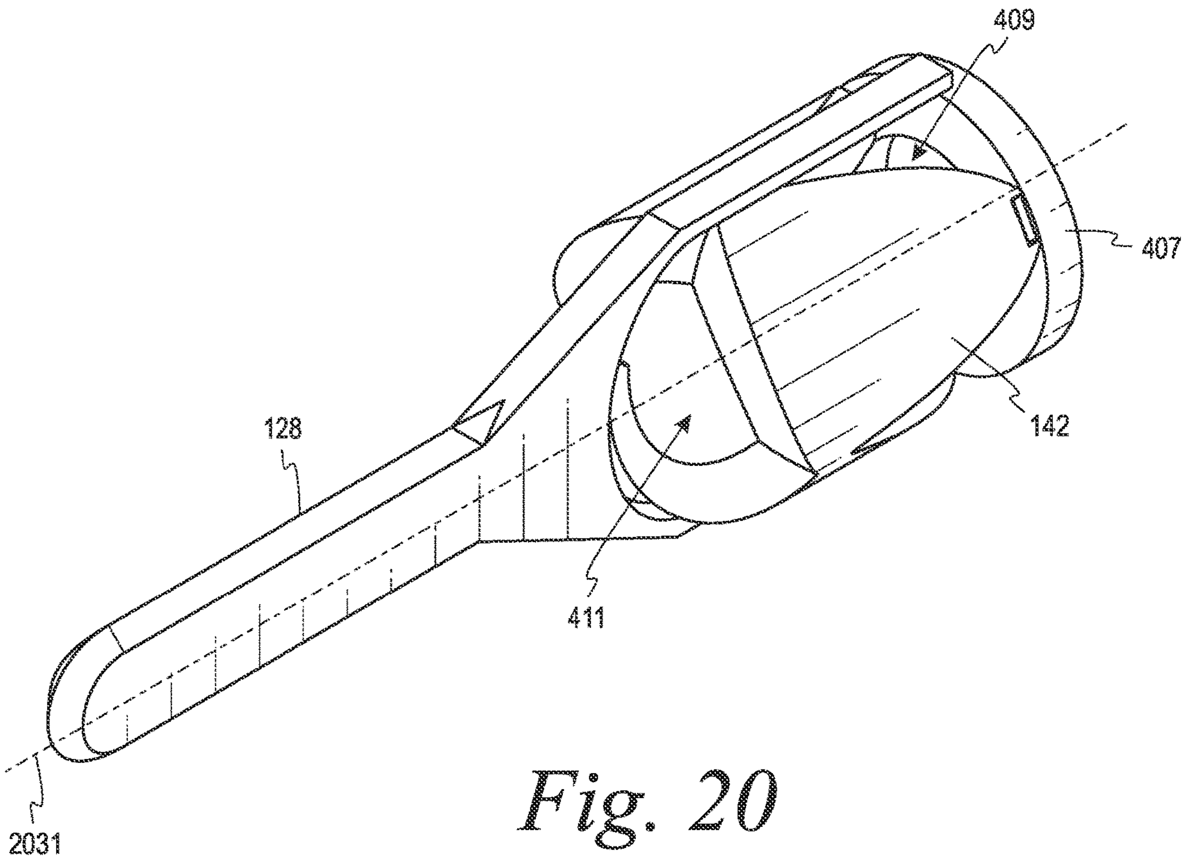
FIG. 20 depicts an assembly of the optical lens assembly of FIGS. 5A-5B and the electrosurgical electrode, according to an example.

FIG. 19 depicts a partially exploded view of an assembly of the light source 140, the optical lens assembly 142 of FIGS. 5A-5B, and a heat sink 1580 on the smoke evacuation channel 148 according to an example. FIG. 20 depicts an assembly of the optical lens assembly 142 shown in FIGS. 5A-5B and the electrosurgical electrode 128.

As shown in FIGS. 15-16 and 19-20, the electrosurgical device 112 can include the light sources 140 and the optical lens assembly 142 in the shaft 126 of the housing 123. As noted above, the light sources 140 are configured to emit light into the optical lens assembly 142, and the optical lens assembly 142 is configured to transmit the light from the light sources 140 in a distal direction and emit the light from the distal end 126B of the shaft 126.

As shown in FIG. 20, the electrosurgical electrode 128 has a longitudinal axis 2031 extending between the proximal end of the electrosurgical electrode 128 and a distal end of the electrosurgical electrode 128. The light sources 140 are arranged circumferentially around the longitudinal axis 2031 of the electrosurgical electrode 128. For example, as shown in FIG. 20, the lens aperture 411 can have a center axis that is collinear with the longitudinal axis 2031 of the electrosurgical electrode 128. Arranging the light sources 140 around the electrosurgical electrode 128 can help to distribute the light around the entire circumference of the electrosurgical electrode 128, which can help to mitigate shadows and provide greater uniformity of illumination in all rotational alignments of the electrosurgical electrode 128 relative to the handle 124 and/or the electrosurgical device 112 relative to the target tissue.

Additionally, the smoke evacuation channel 148 can extend through the lens aperture 411 in the optical lens assembly 142 and the PCB aperture 409 in the LED PCB 407. This can help to locate the smoke evacuation channel 148 at a center of the shaft 126 (e.g., the center axis of the smoke evacuation channel 148 and the center axis of the shaft 126 can be collinear), which can enhance suction at the surgical site. In this arrangement, the electrosurgical device 112 can provide illumination and suction around the circumference of the electrosurgical electrode 128. Further, integrating the optical lens assembly 142 of FIGS. 3 and 5A-5B in this arrangement can improve a quality of illumination, reduce a size of the distal end of the electrosurgical device, and improve a line of sight to the surgical site.

In an example, the light source 140, the optical lens assembly 142, and/or the heat sink 1580 can be fixedly coupled to the handle 124. In this arrangement, the shaft 126 and the electrosurgical electrode 128 can rotate about the light source 140, the optical lens assembly 142, and/or the heat sink 1580. For instance, the light source 140, the optical lens assembly 142, and/or the heat sink 1580 can have a non-circular shape that can engage with a non-circular shape of the body 148C of the smoke evacuation channel 148 to inhibit rotation of the light source 140, the optical lens assembly 142, and/or the heat sink 1580 relative to the handle 124 while the shaft 126 and the electrosurgical electrode 128 rotate relative to the handle 124. In FIGS. 19-20, the non-circular shape is an oval shape. However, the light source 140, the optical lens assembly 142, the heat sink 1580, and/or the smoke evacuation channel 148 can have other non-circular shapes in other examples.

Additionally, in this arrangement, the light source 140, the optical lens assembly 142, and the heat sink 1580 can be telescopically movable together with the shaft 126 relative to the handle 124. As noted above, the housing conductor 134 and the shaft conductor 136 can provide for electrically coupling the light source 140 to the DC power source 144 during such telescopic movement. As shown in FIG. 19, the shaft 126 can include a positive-light electrical conductor 1536A and a negative-light electrical conductor 1536B that slidably engage corresponding electrical conductors in the handle 124 while the shaft 126 telescopically moves in an axial direction relative to the handle 124.

Figure 21:
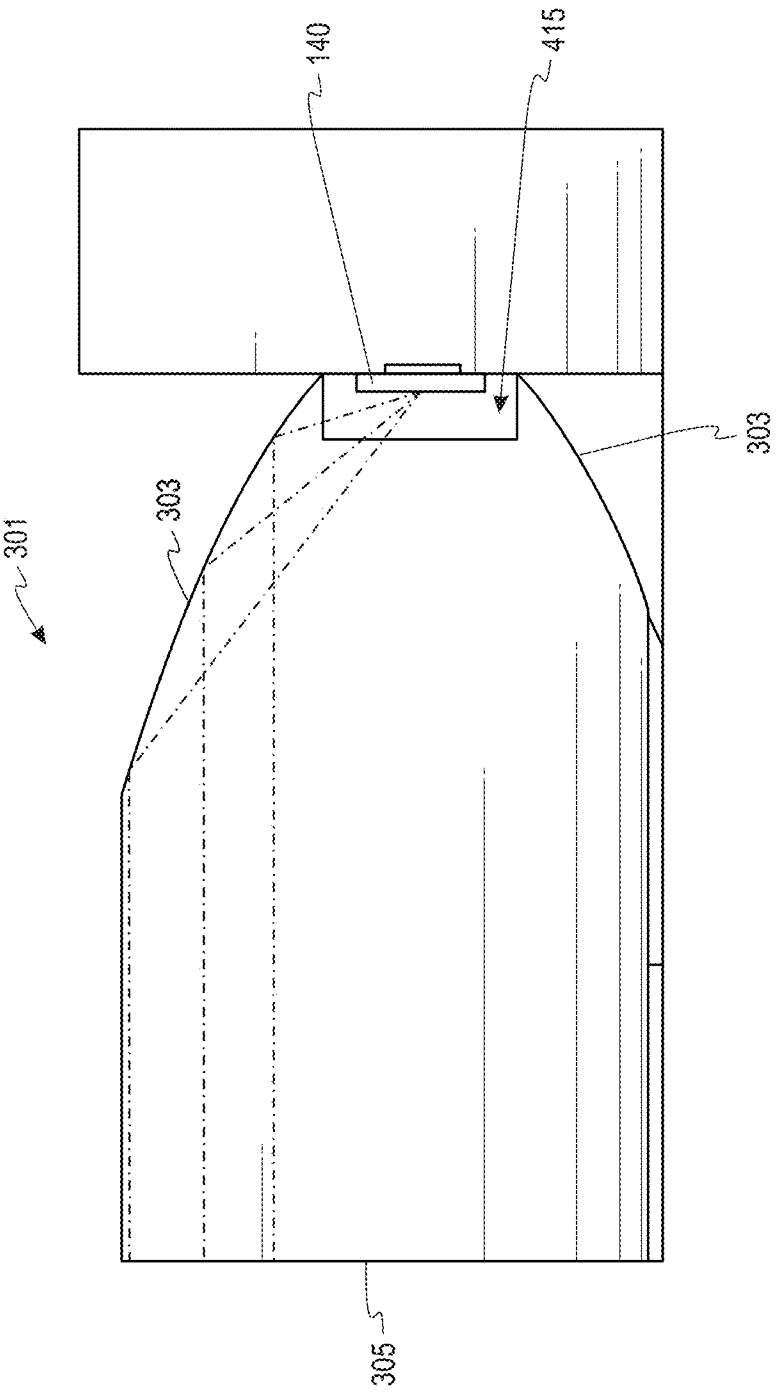
FIG. 21 depicts a cross-sectional view of an optical component of the optical lens assembly shown in FIG. 3 is illustrated, according to an example.

Referring now to FIG. 21, a cross-sectional view of an optical component 301 of the optical lens assembly 142 shown in FIG. 3 is illustrated according to an example. As shown in FIG. 21, the optical lens assembly 142 includes a proximal reflector surface 303 having an aspheric shape and a distal transmission surface 305. Additionally, FIG. 21 depicts the light source 140 received in the cavity 415 of the optical component 301 at the proximal end 142A. FIG. 21 further depicts ray traces showing example light rays emitted by the light source 140, which are reflected and collimated by the proximal reflector surface 303 as the light rays propagate to the distal transmission surface 305.

Figure 22:
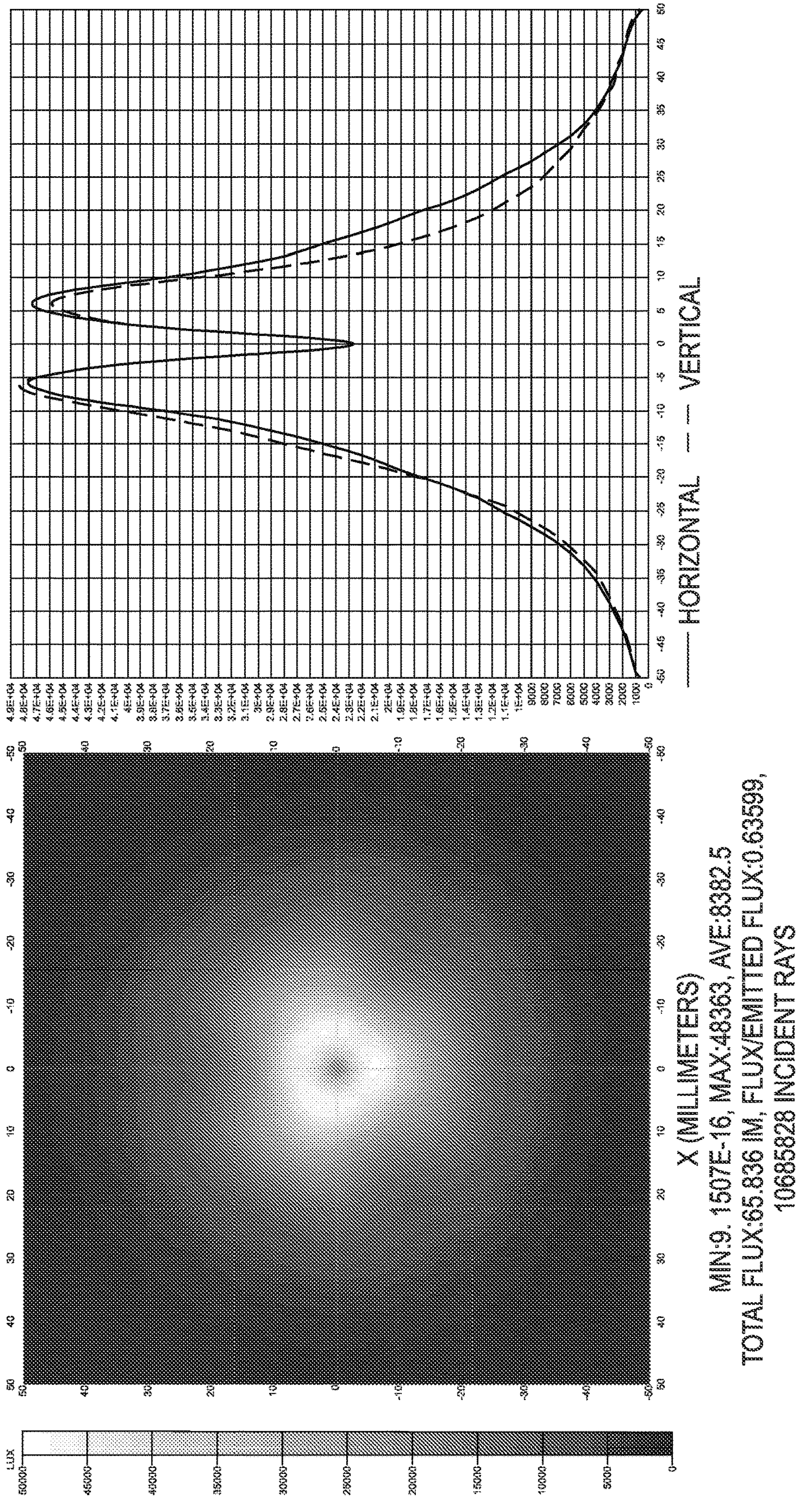
FIG. 22 depicts an optical output pattern for the optical lens assembly shown in FIGS. 4A-4B, according to an example.
Figure 23:
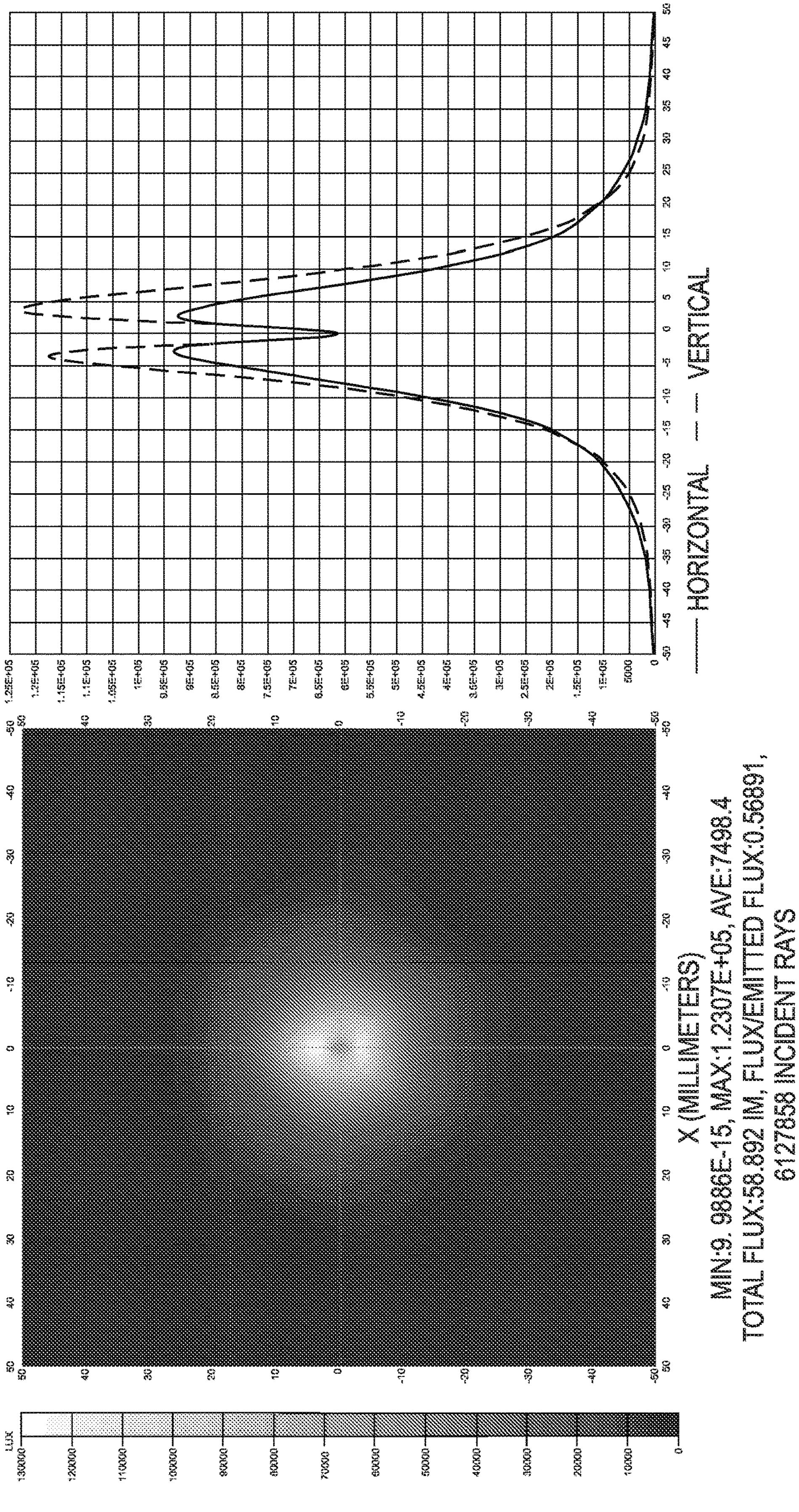
FIG. 23 depicts an example optical output pattern for the optical lens assembly shown in FIGS. 5A-5B, according an example.

FIG. 22 depicts an example optical output pattern for the optical lens assembly 142 shown in FIGS. 4A-4B and FIG. 23 depicts an example optical output pattern for the optical lens assembly 142 shown in FIGS. 5A-5B, according examples.

Figure 24:
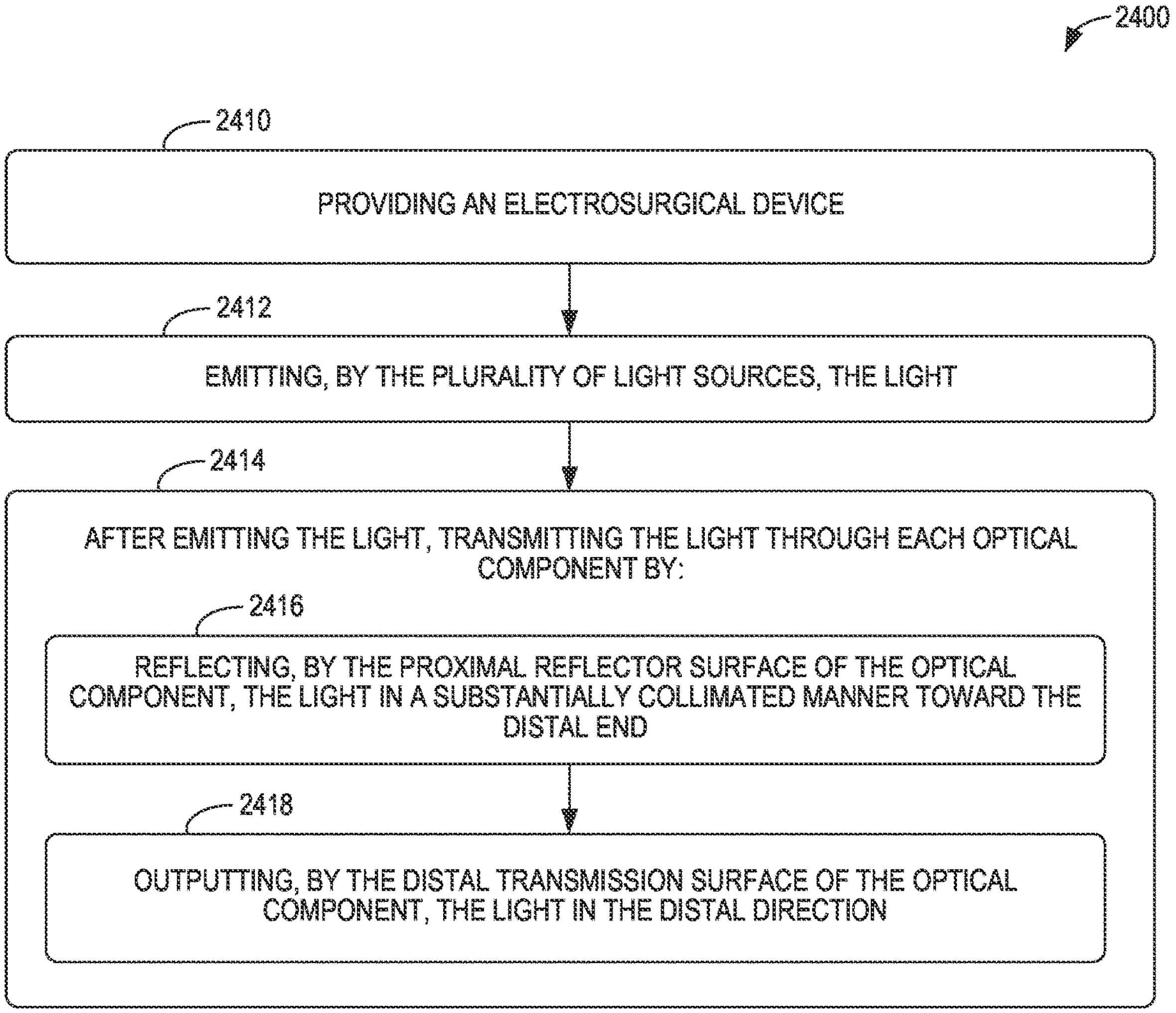
FIG. 24 illustrates a flow chart of an example process for operating an electrosurgical device, according to an example.

Referring now to FIG. 24, a flowchart of a process 2400 of operating an electrosurgical device is shown according to an example. As shown in FIG. 24, the process 24 can include providing an electrosurgical device at block 2410. The electrosurgical device can include a housing having a proximal end and a distal end. The electrosurgical device can also include an electrosurgical electrode extending in a distal direction from the distal end of the housing, and a plurality of light sources in the housing. The plurality of light sources can be configured to generate light.

Additionally, the electrosurgical device can include an optical lens assembly having a proximal end and a distal end. The optical lens assembly can include a plurality of optical components that are (i) coupled to each other at the distal end of the optical lens assembly and (ii) separated from each other at the proximal end of the optical lens assembly. Each optical component is optically coupled to a respective light source of the plurality of light sources. Each optical component includes a proximal reflector surface extending distally from the respective light source that is optically coupled to the optical component and a distal transmission surface at the distal end of the optical lens assembly. The proximal reflector surface is configured to reflect light emitted by the respective light source toward the distal end. The proximal reflective surface can have an aspheric shape that is configured to substantially collimate the light reflected by the proximal reflector surface. The distal transmission surface is configured to output the light from the optical component in the distal direction.

At block 2412, the process 2400 includes emitting, by the plurality of light sources, the light. After emitting the light at block 2412, the process 2400 includes, at block 2414, transmitting the light through each optical component by: (i) reflecting, by the proximal reflector surface of the optical component, the light in a substantially collimated manner toward the distal end at block 2416, and (ii) outputting, by the distal transmission surface of the optical component, the light in the distal direction at block 2418.

Figure 25:
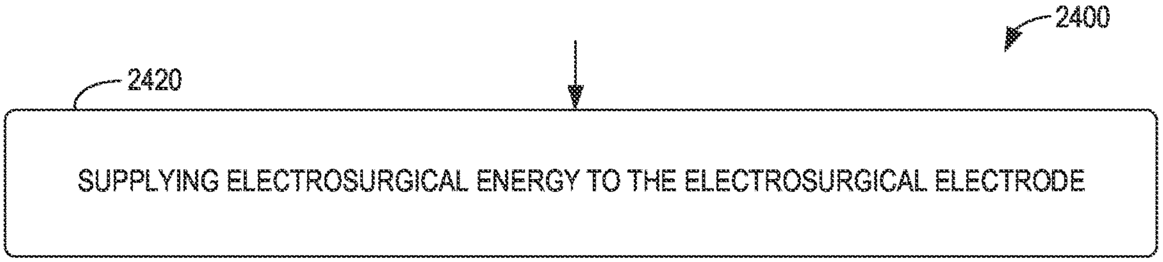
FIG. 25 illustrates a flow chart of an example process for operating an electrosurgical device that can be used with at least the process shown in FIG. 24.

FIGS. 25-30 depict additional aspects of the process 2400 according to further examples. As shown in FIG. 25, the process 2400 can also include supplying electrosurgical energy to the electrosurgical electrode at block 2420. In one example, supplying electrosurgical energy to the electrosurgical electrode at block 2420 can be performed while emitting the light at block 2412.

Figure 26:
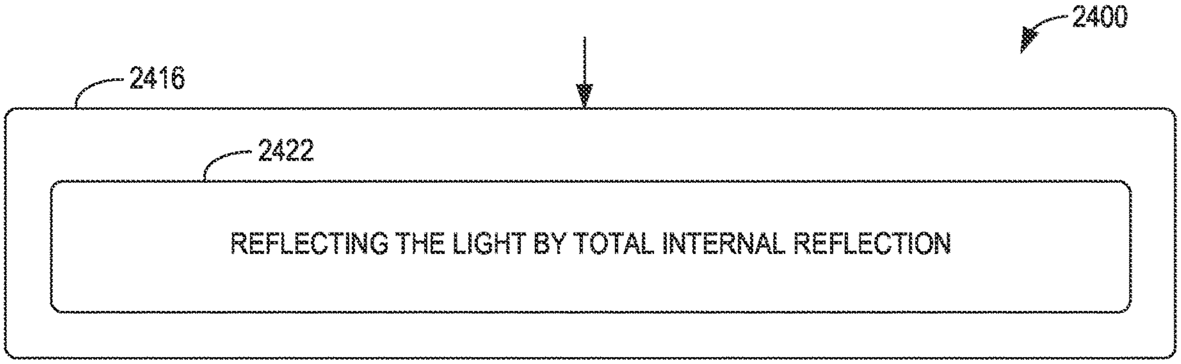
FIG. 26 illustrates a flow chart of an example process for operating an electrosurgical device that can be used with at least the process shown in FIG. 24.

As shown in FIG. 26, reflecting, by the proximal reflector surface, the light at block 2416 can include reflecting the light by total internal reflection at block 2422. In the example shown in FIG. 26, the proximal reflector surface can be a total internal reflection (TIR) reflector.

Figure 27:
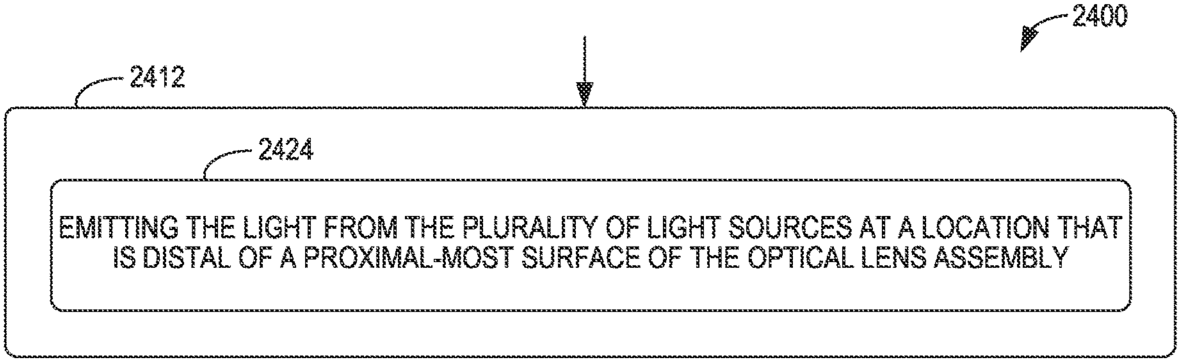
FIG. 27 illustrates a flow chart of an example process for operating an electrosurgical device that can be used with at least the process shown in FIG. 24.

In the example shown in FIG. 27, at the proximal end of the optical lens assembly, each optical component can define an cavity in which the respective light source is located such that the plurality of light sources are distal of a proximal-most surface of the optical lens assembly. As shown in FIG. 27, emitting the light at block 2412 can include emitting the light from the plurality of light sources at a location that is distal of a proximal-most surface of the optical lens assembly at block 2424.

Figure 28:
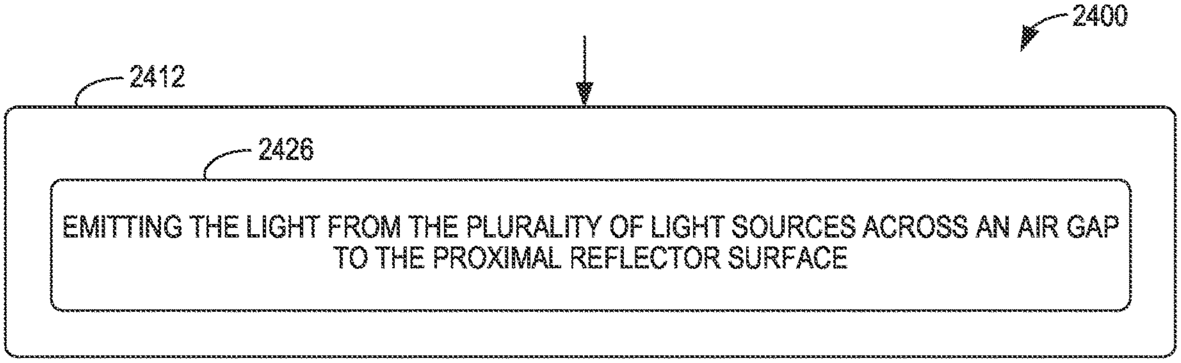
FIG. 28 illustrates a flow chart of an example process for operating an electrosurgical device that can be used with at least the process shown in FIG. 24.

As shown in FIG. 28, emitting the light at block 2412 can include emitting the light from the plurality of light sources across an air gap to the proximal reflector surface at block 2426.

Figure 29:
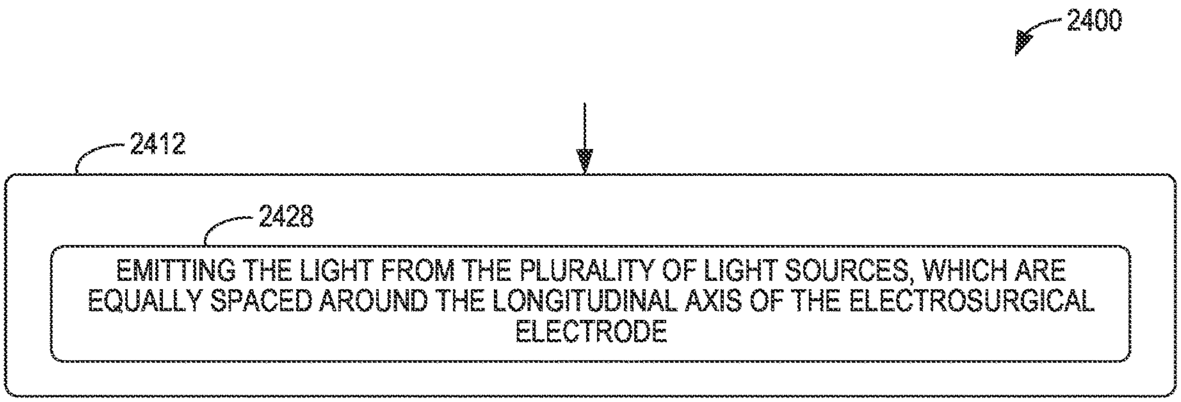
FIG. 29 illustrates a flow chart of an example process for operating an electrosurgical device that can be used with at least the process shown in FIG. 24.

As shown in FIG. 29, emitting the light at block 2412 can include emitting the light from the plurality of light sources, which are equally spaced around the longitudinal axis of the electrosurgical electrode at block 2428.

Figure 30:
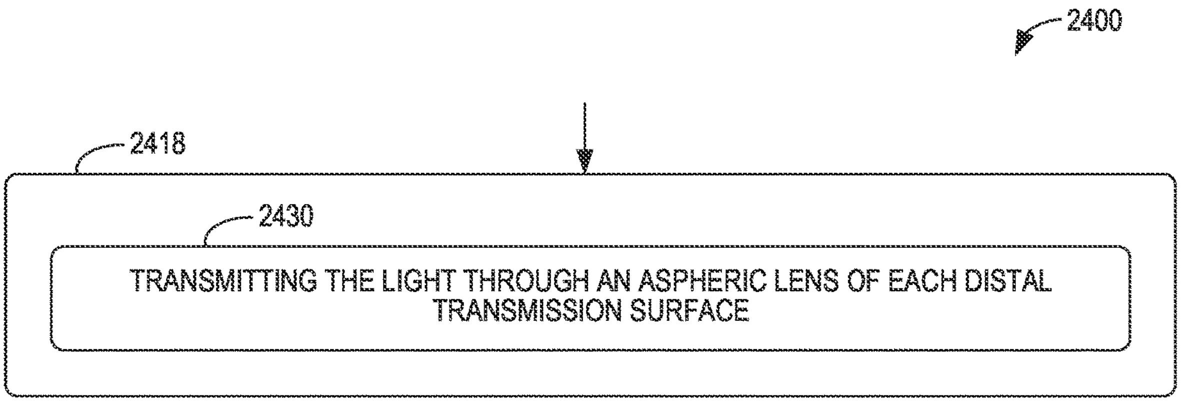
FIG. 30 illustrates a flow chart of an example process for operating an electrosurgical device that can be used with at least the process shown in FIG. 24.

As shown in FIG. 30, outputting, by the distal transmission surface, the light in the distal direction at block 2418 can include transmitting the light through an aspheric lens of each distal transmission surface at block 2430.

Figure 31:
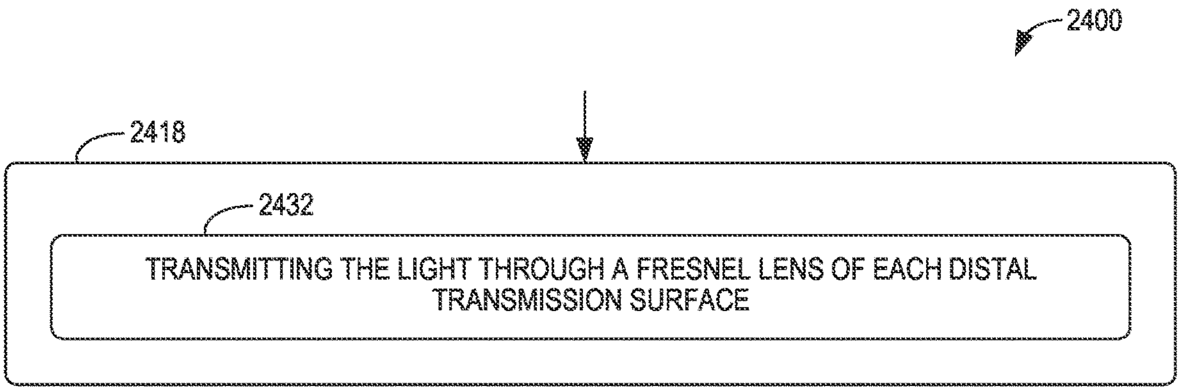
FIG. 31 illustrates a flow chart of an example process for operating an electrosurgical device that can be used with at least the process shown in FIG. 24.

As shown in FIG. 31, outputting, by the distal transmission surface, the light in the distal direction at block 2418 can include transmitting the light through a Fresnel lens of each distal transmission surface at block 2432.

Figure 32:
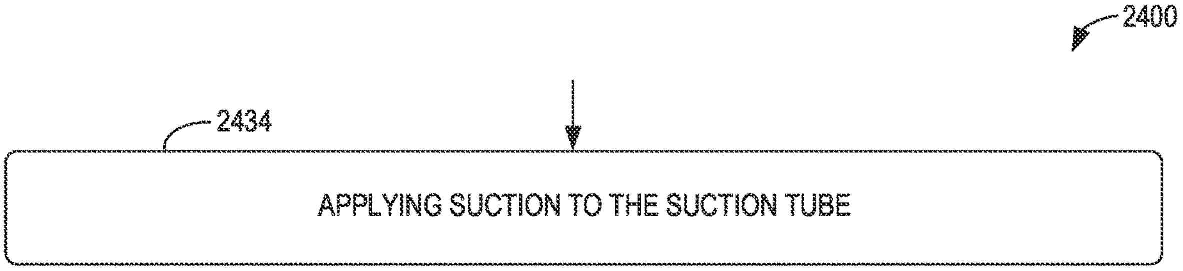
FIG. 32 illustrates a flow chart of an example process for operating an electrosurgical device that can be used with at least the process shown in FIG. 24.

In the example shown in FIG. 32, the plurality of light sources can include a plurality of light emitting diodes (LEDs) coupled to a printed circuit board (PCB). Also, the PCB can include a ring having a PCB aperture. The electrosurgical device can include a suction tube that extends through the PCB aperture in the PCB and an aperture in the optical lens assembly. The plurality of light sources can be located around a circumference of the suction tube. The distal end of the optical lens assembly can extend around the circumference of the suction tube. As shown in FIG. 32, the process 2400 can also include applying suction to the suction tube at block 2434.

Figure 33:
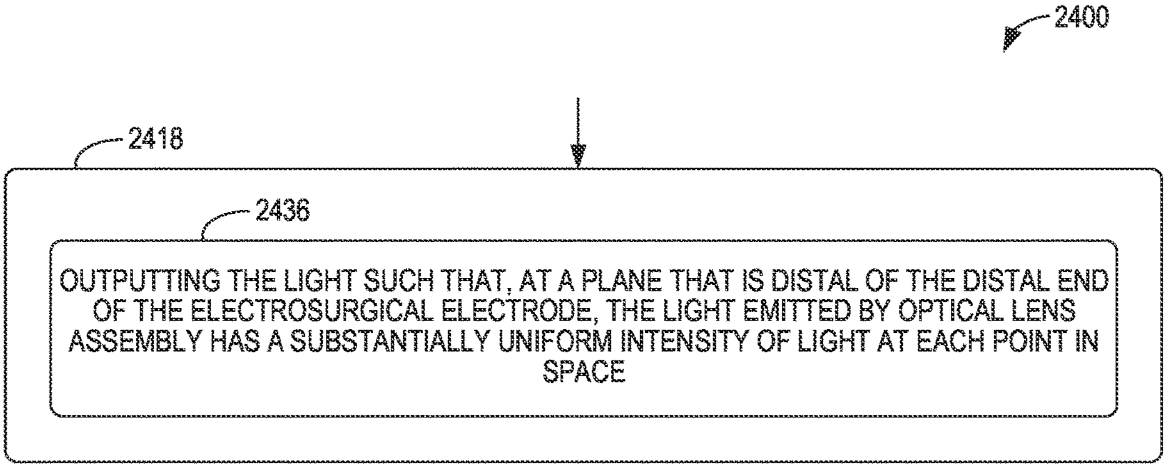
FIG. 33 illustrates a flow chart of an example process for operating an electrosurgical device that can be used with at least the process shown in FIG. 24.

As shown in FIG. 33, outputting the light at block 2418 can include outputting the light such that, at a plane that is distal of the distal end of the electrosurgical electrode, the light emitted by optical lens assembly has a substantially uniform intensity of light at each point in space at block 2436.

Figure 34:
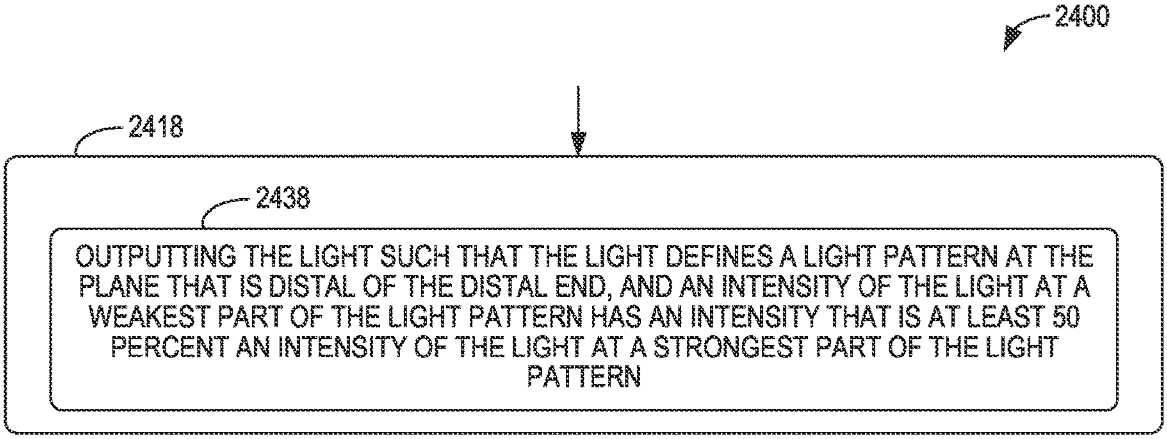
FIG. 34 illustrates a flow chart of an example process for operating an electrosurgical device that can be used with at least the process shown in FIG. 24.

As shown in FIG. 34, outputting the light at block 2418 can include outputting the light such that the light defines a light pattern at the plane that is distal of the distal end, and an intensity of the light at a weakest part of the light pattern has an intensity that is at least 50 percent an intensity of the light at a strongest part of the light pattern at block 2438.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms “a,” “and,” “said,” and “the” include plural referents unless the context clearly dictates otherwise. It is further noted that the claims may be drafted to exclude any optional element. As such, this statement is intended to serve as antecedent basis for use of such exclusive terminology as “solely,” “only” and the like in connection with the recitation of claim elements, or use of a “negative” limitation. Unless defined otherwise herein, all technical and scientific terms used herein have the same meaning as commonly understood by one of ordinary skill in the art, to which this invention belongs. The breadth of the present application is not to be limited by the subject specification, but rather only by the plain meaning of the claim terms employed.

What is claimed is:

1. An electrosurgical device, comprising: a housing having a proximal end and a distal end; an electrosurgical electrode extending in a distal direction from the distal end of the housing; a plurality of light sources in the housing, wherein the plurality of light sources are configured to generate light; and an optical lens assembly having a proximal end and a distal end, wherein the optical lens assembly comprises a plurality of optical components that are (i) coupled to each other at the distal end of the optical lens assembly and (ii) separated from each other at the proximal end of the optical lens assembly, wherein each optical component is optically coupled to a respective light source of the plurality of light sources, and wherein each optical component comprises: a proximal reflector surface extending distally from the respective light source that is optically coupled to the optical component, wherein the proximal reflector surface is configured to reflect light emitted by the respective light source toward the distal end, wherein the proximal reflective surface has an aspheric shape that is configured to substantially collimate the light reflected by the proximal reflector surface, and a distal transmission surface at the distal end of the optical lens assembly, wherein the distal transmission surface is configured to output the light from the optical component in the distal direction, wherein, at the proximal end of the optical lens assembly, each optical component defines an cavity in which the respective light source is located such that the plurality of light sources are distal of a proximal-most surface of the optical lens assembly.

2. The electrosurgical device of claim 1, wherein the proximal reflector surface comprises a total internal reflection (TIR) reflector.

3. The electrosurgical device of claim 2, wherein the proximal reflector surface and the housing are separated from each other such that an air gap surrounds the proximal reflector surface.

4. The electrosurgical device of claim 1, wherein each optical component is separated from the respective light source optically coupled to the optical component by an air gap.

5. The electrosurgical device of claim 1, wherein the electrosurgical electrode has a longitudinal axis extending between a proximal end of the electrosurgical electrode and a distal end of the electrosurgical electrode, and wherein the plurality of light sources are arranged circumferentially around the longitudinal axis of the electrosurgical electrode.

6. The electrosurgical device of claim 5, wherein the plurality of light sources consists of three light sources equally spaced around the longitudinal axis of the electrosurgical electrode.

7. The electrosurgical device of claim 5, wherein optical lens assembly defines an aperture having a center axis that is collinear with the longitudinal axis of the electrosurgical electrode.

8. The electrosurgical device of claim 1, wherein each distal transmission surface is an aspheric lens.

9. The electrosurgical device of claim 1, wherein each distal transmission surface is a Fresnel lens.

10. The electrosurgical device of claim 9, wherein the Fresnel lens has flat surface at a distal end, wherein the flat surface at the distal end defines a plurality of rings that are concentric with each other, and wherein each ring has a respective optical characteristic, and wherein the optical characteristics of the plurality of rings differ from each other such that the flat surface at the distal end transmits light in a manner that approximates an aspheric lens.

11. The electrosurgical device of claim 10, wherein the flat surface at the distal end comprises a plurality of lenslets.

12. The electrosurgical device of claim 1, wherein the optical lens assembly comprises an inner surface and an outer surface, wherein the inner surface defines a through-bore, wherein, between the proximal reflector surface and the distal transmission surface, a cross-section of the optical lens assembly has a non-circular shape at the inner surface and a circular shape at the outer surface.

13. The electrosurgical device of claim 12, wherein the non-circular shape is an elliptical shape.

14. The electrosurgical device of claim 1, wherein less than approximately 10% of light from one optical lens component of the plurality of optical components passes through an adjacent one of the plurality of optical components, wherein a portion of the light emitted by one of the plurality of optical components overlaps with a portion of light emitted by another one of the plurality of optical components.

15. The electrosurgical device of claim 1, wherein the housing comprises:

a handle having a proximal end and a distal end; and a shaft extending from the distal end of the housing, wherein the electrosurgical electrode extends from a distal end of the shaft, and wherein the plurality of light sources are in the shaft.

16. The electrosurgical device of claim 15, wherein the shaft comprises a tube and a sleeve structure that extends distally from the tube, wherein the sleeve structure extends around the optical lens assembly, and wherein each distal transmission surface is distal of a distal-most end of the sleeve structure.

17. The electrosurgical device of claim 15, wherein the plurality of light sources comprise a plurality of light emitting diodes (LEDs) coupled to a printed circuit board (PCB), and wherein the PCB comprises a ring having a PCB aperture.

18. The electrosurgical device of claim 17, wherein further comprising a suction tube that extends through the PCB aperture in the PCB and an aperture in the optical lens assembly, wherein the plurality of light sources are located around a circumference of the suction tube, and wherein the distal end of the optical lens assembly extends around the circumference of the suction tube.

19. The electrosurgical device of claim 1, wherein, at a plane that is distal of the distal end of the electrosurgical electrode, the light emitted by optical lens assembly has a substantially uniform intensity of light at each point in space, wherein the light emitted by the optical lens assembly defines a light pattern at the plane that is distal of the distal end, and wherein an intensity of the light at a weakest part of the light pattern has an intensity that is at least 50 percent an intensity of the light at a strongest part of the light pattern.

* * * * *